United States Patent
Berry et al.

(10) Patent No.: US 9,758,588 B2
(45) Date of Patent: Sep. 12, 2017

(54) BLOCKING REAGENT COMPOSITIONS AND METHODS OF MAKING AND USING THE SAME

(71) Applicant: Becton, Dickinson and Company, Franklin Lakes, NJ (US)

(72) Inventors: Jody Douglas Berry, San Diego, CA (US); Priyal Thakur, Franklin Lakes, NJ (US); Mette Ejrnaes, Franklin Lakes, NJ (US); Paul Waterman, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 85 days.

(21) Appl. No.: 14/500,849

(22) Filed: Sep. 29, 2014

(65) Prior Publication Data
US 2015/0093764 A1    Apr. 2, 2015

Related U.S. Application Data

(60) Provisional application No. 61/899,190, filed on Nov. 2, 2013, provisional application No. 61/884,595, filed on Sep. 30, 2013.

(51) Int. Cl.
*C07K 16/28* (2006.01)
*G01N 33/53* (2006.01)

(52) U.S. Cl.
CPC ..... *C07K 16/2896* (2013.01); *G01N 33/5306* (2013.01); *C07K 2317/565* (2013.01); *C07K 2317/76* (2013.01); *G01N 2333/70596* (2013.01)

(58) Field of Classification Search
CPC .......... C07K 2317/76; C07K 2317/565; C07K 16/00; C07K 16/2896; A61K 2039/505; A61K 2300/00; G01N 33/68; G01N 2333/70596; G01N 33/6854; G01N 33/5306
See application file for complete search history.

(56) References Cited

U.S. PATENT DOCUMENTS

| | | |
|---|---|---|
| 7,387,897 B2 | 6/2008 | Wognum et al. |
| 2006/0121023 A1 | 6/2006 | Weiner et al. |
| 2009/0203038 A1 | 8/2009 | Brophy et al. |
| 2009/0286258 A1 | 11/2009 | Kaur et al. |
| 2010/0239582 A1 | 9/2010 | Humphreys et al. |

OTHER PUBLICATIONS

Rudikoff et al (Proc Nati Acad Sci USA 1982 Voi 79 p. 1979).
Rudikoff et al. (PNAS USA (1982) 79:1979-1983).*
Harlow & Lane ("Antibodies: A Laboratory Manual" (1988) ColdSpring Harbor Laboratory Press, Cold Spring Harbor, New York, pp. 25-26).*
BD Application Handbook ,2003 retrieved from url://research.missouri.edu/cic/files/Immune_Function_Analysis_Techniques.pdf.*

* cited by examiner

*Primary Examiner* — Tracy Vivlemore
*Assistant Examiner* — Carmencita M Belei
(74) *Attorney, Agent, or Firm* — Bret E. Field; Bozicevic, Field & Francis LLP

(57) ABSTRACT

Blocking reagent compositions, as well as methods of making and using the same, are provided. Aspects of the composition include a blocking reagent that binds to the cell surface but does not specifically bind to a targeted first cell surface antigen. Also provided are system and kits that include the compositions.

12 Claims, 11 Drawing Sheets

BLOCKING REAGENT COMPOSITIONS AND METHODS OF MAKING AND USING THE SAME

CROSS-REFERENCE TO RELATED APPLICATIONS

Pursuant to 35 U.S.C. §119 (e), this application claims priority to the filing date of U.S. Provisional Patent Application Ser. No. 61/884,595 filed Sep. 30, 2013, and to the filing date of U.S. Provisional Patent Application Ser. No. 61/899,190 filed Nov. 2, 2013; the disclosures of which applications are herein incorporated by reference.

INTRODUCTION

Antibodies are commonly used to detect antigens on the surface of cells. Many antibodies (e.g., polyclonal antibodies) are "sticky" and bind non-specifically to multiple targets (which may be non-target cell surface antigens), generally creating undesirable background signal. Such background signal can, in turn, lead to alterations in the measurable concentration of an antigen of interest, producing substandard assay results.

Blocking reagents may be employed to at least inhibit non-specific binding (e.g., passive or covalent) of assay components to cell surfaces or solid assay surfaces. Blocking agents may also be employed to inhibit non-specific protein-protein interactions. Importantly, useful blocking agents lack cross reactivity with assay components, and therefore do not disrupt the bonds of the specific interactions that are to be evaluated in the assay.

Blocking reagents finding use in various assays include: detergents, e.g., polysorbate 20 (sold under the trademark TWEEN 20) and polyethylene glycol p-(1,1,3,3-tetramethylbutyl)-phenyl ether (sold under the trademark TRITON X-100); proteins, e.g., bovine serum albumin and whole sera; and polymer based blockers, e.g., polyethylene glycol, polyvinyl and polyvinyl alcohol.

SUMMARY

Blocking reagent compositions, as well as methods of making and using the same, e.g., in immunoassays to reduce background staining, are provided. Also provided are systems and kits that include the compositions.

BRIEF DESCRIPTION OF THE FIGURES

FIG. 9: This figure depicts the nucleic acid sequence (SEQ ID NO:03) and the encoded amino acid sequence (SEQ ID NO:04) of the light chain of a representative monoclonal antibody. The amino acid sequence present within a CDR of the light chain of the anti-CD88 mAb (QSVYNNNLL) (SEQ ID NO:05; FIG. 9) is indicated, where amino acid residues were mutated to residues not typically found to be key in antibody antigen interactions. The boxed sequence indicates the position of amino acids that may be mutated to generate a blocking reagent; highlighted residue provides an example where a single substitution can be made.

FIG. 10: This figure depicts the nucleic acid sequence (SEQ ID NO:06) and the encoded amino acid sequence (SEQ ID NO:07) of the heavy chain of a representative monoclonal antibody. The amino acid sequence present within a CDR of the heavy chain of the anti-CD88 mAb (TYFCRIGSNI) (SEQ ID NO:08; FIG. 10) is indicated, where amino acid residues were mutated to residues not typically found to be key in antibody antigen interactions. The boxed sequence indicates the position of amino acids that may be mutated to generate a blocking reagent; highlighted residue provides an example where a single substitution can be made.

FIG. 11 shows an SDS-PAGE analysis and coomassie staining of the parental (reference) and mutant antibodies described above.

DETAILED DESCRIPTION

Blocking reagent compositions, as well as methods of making and using the same, are provided. Aspects of the compositions include a blocking reagent that binds to the cell surface but does not specifically bind to a targeted first cell surface antigen. Also provided are systems and kits that include the compositions.

Figure 1:
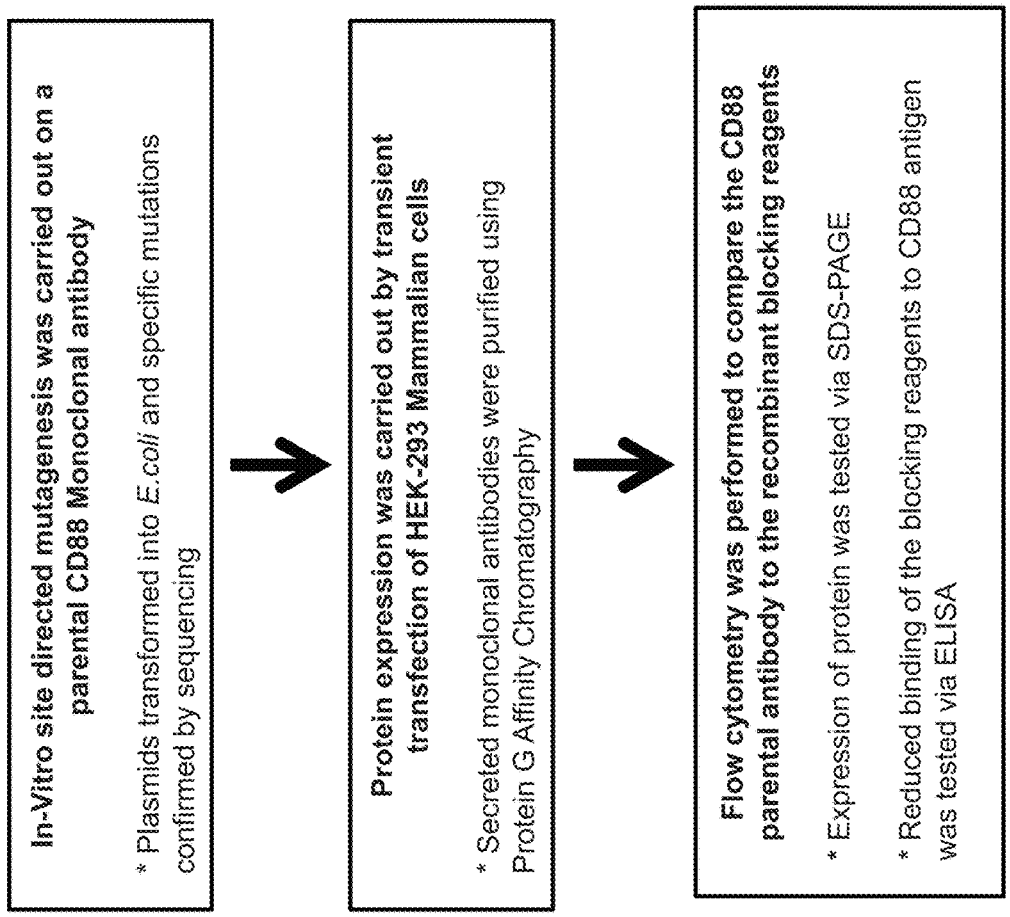
FIG. 1 provides a flow chart for one method for producing a blocking reagent according to one embodiment.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Blocking Compositions and Methods of Making the Same

Aspects of the disclosure include a blocking composition for use with a first specific binding member, e.g., which is known to provide background signal in addition to specific target signal, where the first specific binding member specifically binds to a first cell surface antigen (e.g., a target cell surface antigen for an immunoassay); and the blocking composition includes a blocking reagent. Blocking compositions may include one or more blocking reagents present in a suitable medium, e.g., an aqueous medium, such as described in greater detail below.

Blocking Reagent

As summarized above, blocking compositions of the invention include one or more blocking reagents. The blocking reagents present in the composition may be monoclonal or polyclonal, and in some instances are monoclonal. While a given blocking composition may include 2 or more distinct blocking agents of differing chemical formula, e.g., sequence, such as 3 or more, 4 or more, 5 or more, etc., in some instances a given composition includes a single type of blocking reagent.

As used herein, the term "blocking", "to block" (e.g., as in the phrase "blocking reagent") refers to preventing non-specific binding from occurring, to a target other than the intended target, when using a one or more (e.g., a cocktail) of antibodies and allowing the specific binding to occur. For example, many antibodies bind to non-target antigens (secondary antigens) (e.g., with lower affinity) in addition to the target antigen (the primary antigen) to which they specifically bind with high affinity. Some species of antibody and individual antibodies can have sticky binding characteristics and thus increase background signal. A subject "blocking reagent" is an antibody or binding fragment thereof to be used in conjunction with a specific binding member, where the specific binding member (e.g., an antibody) specifically binds an antigen of interest (a first cell surface antigen). A subject blocking reagent no longer binds to the surface of a cell but is free to bind through its other sticky natural properties and in the case of flow cytometry is unlabeled. This blocker can coat and hence block the cell from being able to be sticky with specific labeled antibody.

As used herein, the term "antigen" includes, but is not limited to, proteins (e.g., peptides), sugars, lipids, glycolipids, etc. An "antigen of interest", "target antigen", and "first cell surface antigen" are herein used interchangeably to refer to an antigen to be detected (e.g., using a first specific binding member).

The terms "specific binding," "specifically binds," and the like, refer to the preferential binding of a molecule (e.g., one binding pair member to the other binding pair member of the same binding pair) relative to other molecules or moieties in a solution or reaction mixture. The term "specific binding member" refers to a member of a specific binding pair. Exemplary specific binding members include, but are not limited to ligand/receptor; antibody/antigen; and the like. Specific binding members can be proteins (e.g., peptides, polypeptides, etc.), fusion proteins, antibodies, etc. In some embodiments, the affinity between a pair of specific binding members when they are specifically bound to each other in a binding complex is characterized by a $K_D$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower Kd.

In some cases, the first specific binding member is an antibody (e.g., monoclonal antibody, polyclonal antibody, etc.) that specifically binds a cell surface antigen (e.g., a cell surface protein). The term "antibody" is used herein in the broadest sense and encompasses monoclonal antibodies (including full length monoclonal antibodies), polyclonal antibodies, multi-specific antibodies (e.g., bispecific antibodies), and antibody fragments so long as they exhibit the desired biological activity. "Antibodies" (Abs) and "immunoglobulins" (Igs) are glycoproteins having the same structural characteristics. Antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, $IgG_1$, $IgG_2$, $IgG_3$, $IgG_4$, $IgA_1$ and $IgA_2$) or subclass.

"Antibody fragment", and all grammatical variants thereof, as used herein are defined as a portion of an intact antibody comprising the antigen binding site and/ror variable region of the intact antibody. Examples of antibody fragments include Fab, Fab', Fab'-SH, F(ab')2, and scFv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules; (2) single chain polypeptides containing only one light chain variable domain, or a fragment thereof that contains the three CDRs of the light chain variable domain, without an associated heavy chain moiety; (3) single chain polypeptides containing only one heavy chain variable region, or a fragment thereof containing the three CDRs of the heavy chain variable region, without an associated light chain moiety; (4) nanobodies comprising single Ig domains from non-human species or other specific single-domain binding modules; and (5) multi-specific or multivalent structures formed from antibody fragments. In an antibody fragment comprising one or more heavy chains, the heavy chain(s) can contain any constant domain sequence (e.g., CH1 in the IgG isotype) found in a non-Fc region of an intact antibody, and/or can contain any hinge region sequence found in an intact antibody.

As used herein, the term "epitope" or "epitopes" refers to sites or fragments of a polypeptide or protein having antigenic or immunogenic activity in a subject. An epitope having immunogenic activity is a site or fragment of a polypeptide or protein that elicits an antibody response in an animal. An epitope having antigenic activity is a site or fragment of a polypeptide or protein to which an antibody (e.g, via the antigen binding site) specifically binds. Epitopic determinants can consist of chemically active surface groupings of molecules such as amino acids or sugar side chains and usually have specific three dimensional structural characteristics, as well as specific charge characteristics.

Suitable antibodies can be generated by any animal (e.g., a bird (e.g., duck, chicken, goose, etc.); a shark; a fish (e.g., zebrafish); a mammal (e.g., a non-primate, e.g., cow, pig, camel, llama, horse, goat, rabbit, sheep, hamster, guinea pig, pig, cat, dog, rat, mouse, etc.; a non-human primate, e.g., monkey, cynomolgus monkey, chimpanzee, etc; a human; etc.), and the like. Similarly suitable blocking reagents with specific binding removed, can be made as blockers for each species.

Antibodies can be humanized. The term "humanized" antibody refers to an immunoglobulin variant or fragment thereof, which is capable of binding to an antigen and which comprises framework regions having substantially the amino acid sequence of a human immunoglobulin and CDRs having substantially the amino acid sequence of a non-human antibody. A humanized antibody can be fully or partially humanized.

Reference Antibody

Blocking reagents of interest include antibodies or binding fragments thereof that are variants of a reference antibody. Thus, in some instances a blocking reagent is an antibody or binding fragment thereof that includes at least one mutation (e.g., deletion, insertion, substitution, etc.) in at least one of: a heavy chain complementary determining ("CDR") region (for example, the heavy chain CDR 1, heavy chain CDR 2, and/or heavy chain CDR 3); and a light chain CDR region (for example, the light chain CDR 1, light chain CDR 2, and/or light chain CDR 3) when compared to the amino acid sequence of the reference antibody. Moreover, a subject blocking reagent may also contain one or more other mutations (e.g., deletion, insertion, substitution, etc.) in a part or portion other than a CDR region (e.g., in a framework region). Methods for creating such derivatives (i.e., variants of a reference antibody) include the use of site-directed mutagenesis and PCR-mediated mutagenesis, or gene construction from a suitable commercial supplier (e.g., GenArt), which will be discussed in more detail below.

The reference antibody specifically binds a second cell surface antigen (an antigen other than the antigen of interest) and the blocking reagent binds with reduced affinity to the second cell surface antigen (reduced relative to the affinity with which the reference antibody binds the second cell surface antigen), and in some instances does not specifically bind to the second cell surface antigen.

Therefore, in some embodiments, at least one CDR of a subject blocking reagent is a variant of the corresponding CDR of a reference antibody, where the reference antibody specifically binds to a second cell surface antigen (i.e., the reference antibody binds to a different cell surface antigen than is specifically bound by first the specific binding member). In some cases, a subject blocking reagent does not specifically bind to the second cell surface antigen (the antigen bound by the reference antibody). In some cases, a subject blocking reagent binds to the second cell surface antigen (the antigen bound by the reference antibody), but binds to the second cell surface antigen with reduced affinity compared to the affinity with which the reference antibody binds to the second cell surface antigen.

In some cases, at least one CDR of the blocking reagent has an amino acid sequence that is 60% or more identical (e.g., 65% or more, 70% or more, 75% or more, 80% or more, 85% or more, 90% or more, 95% or more, 98% or more, 99% or more, 99.5% or more, or 100% identical) to the corresponding CDR amino acid sequence of the reference antibody.

In some cases, the first, second, and third heavy chain CDRs, and the first, second, and third light chain CDRs of the blocking reagent each has an amino acid sequence that is 60% or more identical (e.g., 65% or more, 70% or more, 75% or more, 80% or more, 85% or more, 90% or more, 95% or more, 98% or more, 99% or more, 99.5% or more, etc.) to the corresponding CDR amino acid sequence of the reference antibody.

In some cases, at least one CDR of the blocking reagent has an amino acid sequence that includes 10 or fewer, such as 9 or fewer, 8 or fewer, 7 or fewer 6 or fewer, 5 or fewer, 4 or fewer, 3 or fewer, 2 or fewer amino acid changes, where there may be just a single amino acid change, as compared to the corresponding CDR amino acid sequence of the reference antibody. In some cases, the first, second, and third heavy chain CDRs, and the first, second, and third light chain CDRs of the blocking reagent each has an amino acid sequence having an amino acid sequence that includes 10 or fewer, such as 9 or fewer, 8 or fewer, 7 or fewer 6 or fewer, 5 or fewer, 4 or fewer, 3 or fewer, 2 or fewer amino acid changes, where there may be just a single amino acid change, compared to the corresponding CDR amino acid sequence of the reference antibody. However, in all cases, a subject blocking reagent has at least 1 amino acid change (deletion, insertion, substitution) in at least one CDR amino acid sequence compared to the corresponding CDR amino acid sequence of the reference antibody. For example, the amino acid change in at least one CDR can be the substitution of 10 or fewer amino acids provided in a region of at least one heavy chain CDR corresponding to SEQ ID NO:7 shown in FIG. 10. SEQ ID NO:07 is the heavy chain from a reference rabbit anti-human CD88 antibody: MACPGFLWAL VISTCLEFSM AQSVKESEGG LFKPADTLTL TCTVSGFSVN NKGVMWVRQA PGNGLEWIGS IGISGRVTYA TWAKSRSTIT RDTNLNTVTL KVTSLTVADT ATYFCRIGSN IWGPGTLVTV SSGQPKAPSV FPLAPCCGDT PSSTVTLGCL VRGYLPEPVT VTWNSGTLTN GVRTFPSVRQ SSGLYSLSSV VSVTSSSQPV TCNVAHPATN TKVDKTVAPS TCSKPTCPPP ELLGGPSVFI FPPRPKDTLM ISRTPEVTCV WDVSQDDPE VQFTWYINNE QVRTARPPLR EQQFNSTIRV VSTLPIAHQD WLRGKEFKCK VHNKALPAPI EKTISKARGQ PLEPKVYTMG PPREELSSRS VSLTCMINGF YPSDISVEWE KNGKAEDNYK TTPAVLDSDG SYFLYSKLSV PTSEWQRGDV FTCSVMHEAL HNHYTQKSIS RSPGK (SEQ ID NO:7). The 7 or fewer amino acids can be encompassed in a region within SEQ ID NO:7 e.g., TYFCRIGSNI (SEQ ID NO: 08). The boxed sequence is within CDR-H3

Figure 9:
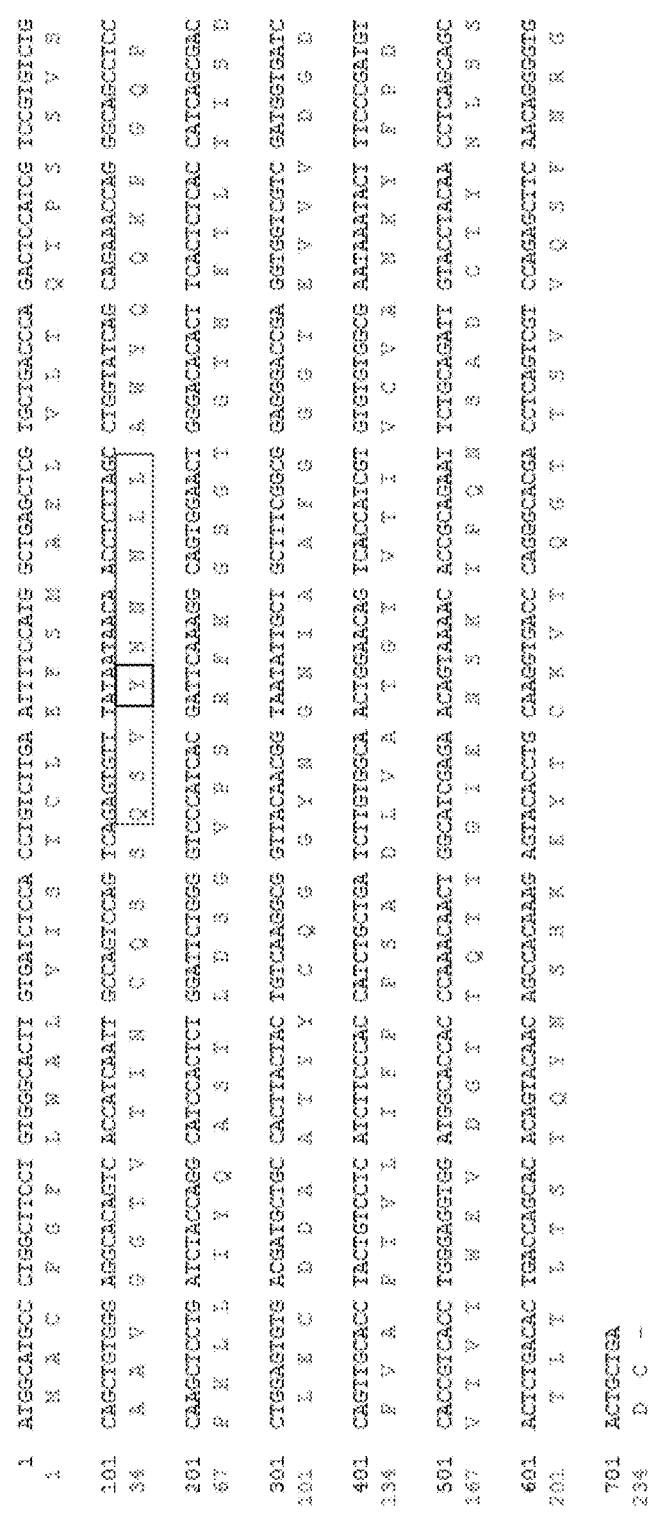

In another example, the amino acid change in at least one CDR can be the substitution of 7 or fewer amino acids provided in a region of at least one light chain CDR corresponding to SEQ ID NO:4 shown in FIG. 9. SEQ ID NO:04 is the light chain from a reference rabbit anti-human CD88 antibody: MACPGFLWALVISTCLEFSM AELVLTQTPSSVSAAVGGTVTINCQSSQSV YNNNLLAWYQQKPGQPPKLLIYQASTLDSG VPSRFKGSGT GTHFTLTISD LECDDAATYY CQGGYNGNGIAAFGGGTEVVVDGDPVAPTVLIFPPSADLV ATGTVTIVCVANKYFPDVTVTWEVDGTTQTTGIENSKTPQNSADCTYNLS STLTLTSTQYNSHKEYTCKVTQGTTSVVQSFNRGDC (SEQ ID NO:04). The 7 or fewer amino acids can be encompassed in a region within SEQ ID NO:04 e.g., QSVYNNNLL (SEQ ID NO: 05). The boxed sequence is within CDR-L1.

Figure 10:
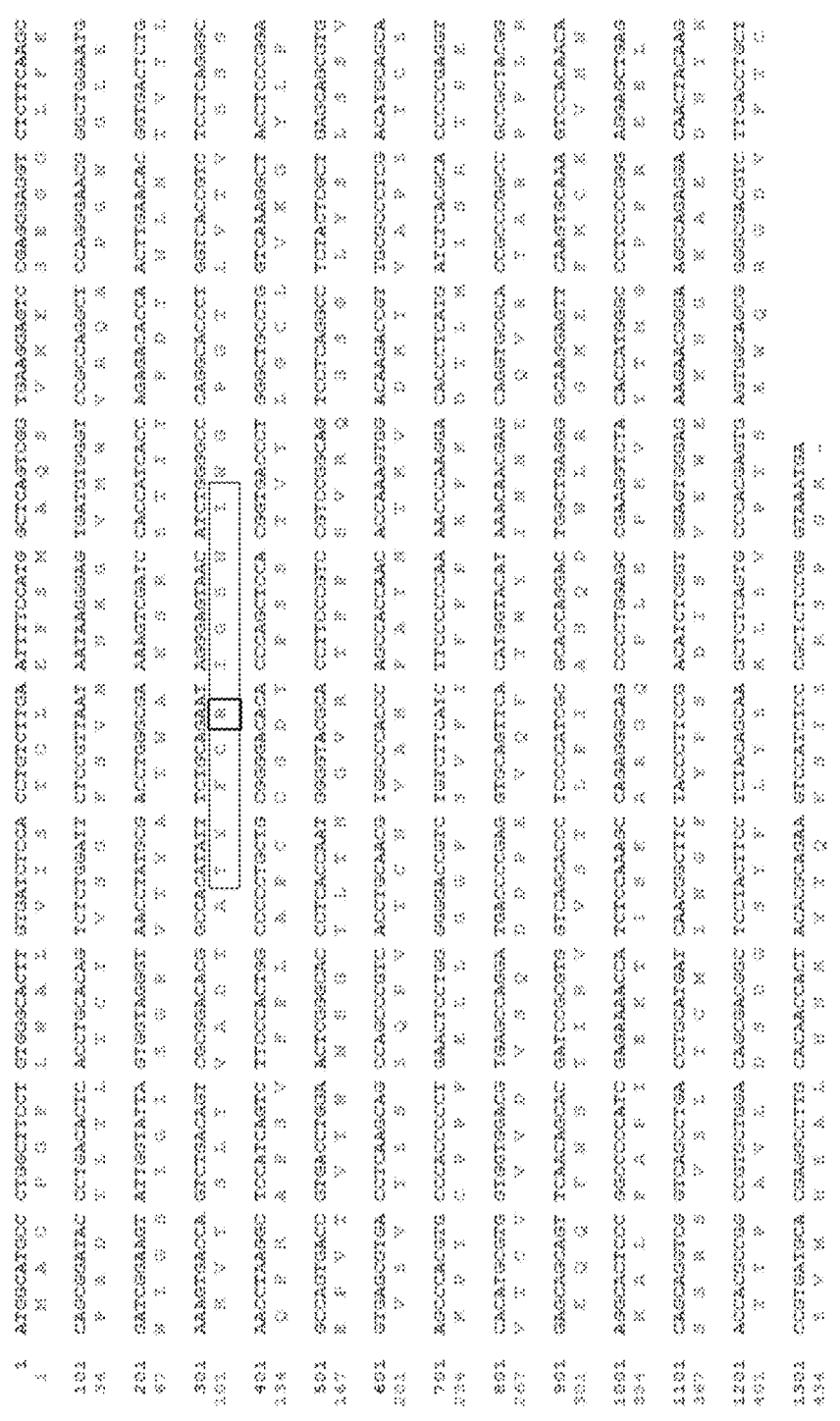

In yet another example, at least one amino acid change in at least one CDR can be a substitution of 7 or fewer amino acids provided in at least one heavy chain CDR corresponding to SEQ ID NO:07 shown in FIG. 10, in combination with the substitution of 7 or fewer amino acids provided in a region of at least one light chain CDR corresponding to SEQ ID NO:04 shown in FIG. 9. In some cases, the combination of at least one substitution in at least one CDR heavy chain and at least one CDR light chain can be made in SEQ ID NO:08 and SEQ ID NO:05, respectively. The effect of at least one amino acid substitution in one or both heavy and light CDRs of a representative blocking reagent are illustrated in FIGS. 4-8. In some cases, the amino acid changes within CDR regions can be combined with amino acid changes outside of the CDR domains.

In some cases, a single amino acid substitution is made in the heavy chain CDR. In other cases, a single amino acid substitution is made in the light chain CDR. In yet other cases, a single amino acid substitution is made in the heavy chain CDR in combination with a single amino acid substitution that is made in the light chain CDR. For example, an amino acid corresponding to R116 of the heavy chain CDR (FIG. 10) can be made alone or in combination with an amino acid substitution of an amino acid corresponding to Y51 of the light chain CDR (FIG. 9). An example of a blocking reagent is a rabbit anti human CD88 antibody comprising a heavy chain CDR having at least one amino acid substitution. Alternatively, the rabbit anti human CD88 antibody blocking reagent comprises a light chain CDR having at least one amino acid substitution. In some cases, the recombinant rabbit anti human CD88 antibody blocking reagent comprises at least one amino acid substitution in at least one light chain CDR and at least one amino acid substitution in at least one heavy chain CDR. The at least one amino acid substitutions can be made for example, within the amino acid sequence of SEQ ID NO:5 of the light chain CDR, and/or the amino acid sequence of SEQ ID NO:8 of the heavy chain CDR. In some cases, the rabbit anti human CD88 antibody blocking reagent comprises the amino acid substitution R116A in the heavy chain CDR shown in FIG. 10. In other cases, the rabbit anti human CD88 antibody comprises the amino acid substitution Y51A in the light chain CDR shown in FIG. 9. Alternatively, the substitution of the Y51 is made to Y51F. In other cases, the rabbit anti human CD88 antibody blocking reagent comprises the R116A substitution in the CDR of the heavy chain and the Y51A or Y51F substitution in the light chain CDR. The rabbit anti human CD88 antibody blocking reagent can further comprise one or more mutations e.g. amino acid substitutions that lie outside of the CDR domains.

In some cases, the non-CDR regions of one of the heavy and light chains of the blocking reagent has an amino acid sequence that is 75% or more identical to the non-CDR regions of the corresponding chain of the reference antibody (e.g., 80% or more identical, 85% or more identical, 90% or more identical, 95% or more identical, 98% or more identical, 99% or more identical, 99.5% or more identical, or 100% identical).

In some cases, the blocking reagent has an amino acid sequence that is 75% or more identical to the non-CDR regions of the corresponding heavy and light chains of the reference antibody (e.g., 80% or more identical, 85% or more identical, 90% or more identical, 95% or more identical, 98% or more identical, 99% or more identical, 99.5% or more identical, or 100% identical). The terms "identical" or percent "identity," in the context of two or more nucleic acids or polypeptide sequences, refer to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection.

For sequence comparison, typically one sequence acts as a reference sequence, to which test sequences are compared. When using a sequence comparison algorithms test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence (e.g., a TERT promoter sequence of the invention as set forth by. e.g., SEQ ID NO: 1 or SEQ ID NO: 2) is compared to another sequence to determine the percent sequence identity relationship (i.e., that the second sequence is substantially identical and within the scope of the invention) using the following parameters: default gap weight (3.00), default gap length weight (0.10), and weighted end gaps. PILEUP can be obtained from the GCG sequence analysis software package, e.g., version 7.0 (Devereaux (1984) Nuc. Acids Res. 12:387-395).

Another example of algorithm that is suitable for determining percent sequence identity (i.e., substantial similarity or identity) is the BLAST algorithm, which is described in Altschul (1990) J. Mol. Biol. 215:403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see, e.g., Henikoff (1989) Proc. Natl. Acad. Sci. USA 89:10915).

The BLAST algorithm also performs a statistical analysis of the similarity between two sequences (see, e.g., Karlin (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Anti-CD88 Antibody

In some cases, the second cell surface antigen (that cell surface antigen to which the reference antibody specifically binds) is CD88. CD88 is a cell surface protein also known as "complement component 5a receptor 1" (C5AR1). Human CD88 has an amino acids sequence:

(SEQ ID NO: 01)
MNSFNYTTPDYGHYDDKDTLDLNTPVDKTSNTLRVPDILALVIFAVV
FLVGVLGNALVVWVTAFEAKRTINAIWFLNLAVADFLSCLALPILFT
SIVQHHHWPFGGAACSILPSLILLNMYASILLLATISADRFLLVFKP
IWCQNFRGAGLAWIACAVAWGLALLLTIPSFLYRVVREEYFPPKVLC
GVDYSHDKRRERAVAIVRLVLGFLWPLLTLTICYTFILLRTWSRRAT
RSTKTLKVVVAVVASFFIFWLPYQVTGIMMSFLEPSSPTFLLLNKLD
SLCVSFAYINCCINPIIYVVAGQGFQGRLRKSLPSLLRNVLTEESVV
RESKSFTRSTVDTMAQKTQAV.

The human DNA nucleotide sequence for an mRNA that encodes the CD88 protein is (the open reading frame is underlined):

(SEQ ID NO: 02)
CTTGGGCAGGAGGGACCTTCGATCCTCGGGGAGCCCAGGAGACCAGAAC<u>ATG
AACTCCTTCAATTATACCACCCCTGATTATGGGCACTATGATGACAAGGATACC
CTGGACCTCAACACCCCTGTGGATAAAACTTCTAACACGCTGCGTGTTCCAGAC
ATCCTGGCCTTGGTCATCTTTGCAGTCGTCTTCCTGGTGGGAGTGCTGGGCAA
TGCCCTGGTGGTCTGGGTGACGGCATTCGAGGCCAAGCGGACCATCAATGCC
ATCTGGTTCCTCAACTTGGCGGTAGCCGACTTCCTCTCCTGCCTGGCGCTGCC
CATCTTGTTCACGTCCATTGTACAGCATCACCACTGGCCCTTTGGCGGGGCCG
CCTGCAGCATCCTGCCCTCCCTCATCCTGCTCAACATGTACGCCAGCATCCTG
CTCCTGGCCACCATCAGCGCCGACCGCTTTCTGCTGGTGTTTAAACCCATCTG
GTGCCAGAACTTCCGAGGGGCCGGCTTGGCCTGGATCGCCTGTGCCGTGGCT
TGGGGTTTAGCCCTGCTGCTGACCATACCCTCCTTCCTGTACCGGGTGGTCCG
GGAGGAGTACTTTCCACCAAAGGTGTTGTGTGGCGTGGACTACAGCCACGACA
AACGGCGGGAGCGAGCCGTGGCCATCGTCCGGCTGGTCCTGGGCTTCCTGTG
GCCTCTACTCACGCTCACGATTTGTTACACTTTCATCCTGCTCCGGACGTGGAG
CCGCAGGGCCACGCGGTCCACCAAGACACTCAAGGTGGTGGTGGCAGTGGTG
GCCAGTTTCTTTATCTTCTGGTTGCCCTACCAGGTGACGGGGATAATGATGTCC
TTCCTGGAGCCATCGTCACCCACCTTCCTGCTGCTGAATAAGCTGGACTCCCT
GTGTGTCTCCTTTGCCTACATCAACTGCTGCATCAACCCCATCATCTACGTGGT
GGCCGGCCAGGGCTTCCAGGGCCGACTGCGGAAATCCCTCCCCAGCCTCCTC
CGGAACGTGTTGACTGAAGAGTCCGTGGTTAGGGAGAGCAAGTCATTCACGCG
CTCCACAGTGGACACTATGGCCCAGAAGACCCAGGCAGTGTAG</u>GCGACAGCC
TCATGGGCCACTGTGGCCCGATGTCCCCTTCCTTCCCGGCCATTCTCCCTCTT
GTTTTCACTTCACTTTTCGTGGGATGGTGTTACCTTAGCTAACTAACTCTCCTCC
ATGTTGCCTGTCTTTCCCAGACTTGTCCCTCCTTTTCCAGCGGGACTCTTCTCA
TCCTTCCTCATTTGCAAGGTGAACACTTCCTTCTAGGGAGCACCCTCCCACCCC
CCACCCCCCCACACACACCATCTTTCCATCCCAGGCTTTTGAAAAACAAACAG
AAACCCGTGTATCTGGGATATTTCCATATGGCAATAGGTGTGAACAGGGAACTC
AGAATACAGACAAGTAGAAAGATTCTCGCTTAAAAAAAATGTATTTATTTTATGG
CAAGTTGGAAAATATGTAACTGGAATCTCAAAAGTTCTTTGGGACAAAACAGAA
GTCCATGGAGTTATCTAAGCTCTTGTAAGTGAGTTAATTTAAAAAAGAAAATTAG
GCTGAGAGCAGTGGCTCACGCCTGTAATCCCAGAACTTTGGGAGGCTAAGGTG
GGTGGATCACCTGAGGTCAAGAGTTCCAGACCAGGCTGGCCAGCATGGTGAA
ACCCCGTCTGTACTAAAAATACAAAAAATTAACTGGGCATGGTAGTGGGTGCCT

```
-continued
GTAATCCCAGCTACTTGGGAGGCTGAGGTGGGAGAATTGCTCGAACTTGGAGG

TGGAGGTTGTGGTGAGCCATGATCGCACCACTGCACTCTAGCCTGGGTGACCG

AGGGAGGCTCTGTCTCAAAAGCAAAGCAAAAACAAAAACAAAAACACCTAAAAA

ACCTGCAGTTTTGTTTGTACTTTGTTTTTAAATTATGCTTTCTATTTTGAGATCAT

TGCAAACTCAACACAATTGTAAGTAATGATACAGAGGGATCTTGTGTACCCTTC

ACCCAGCCTCCCCCAATGGCAACATCTTGCAAAACTACAATGTAGTCTCATAAC

CAGGATATTGACATTGATACAGTGAAGATACAGGACATTCTCATCACCACAGGG

ATCCCCAGGATGCCCACTTCCCTCCACCCCCACACCCCAGCCGTGTCCCTAAC

CCCTGGCAACCAGGAATCCACTCTCCATTTCTATAATGTTGTCATTTCAAGAATG

TTATTCAATGGAATCATATAGTATGTAACCTGTTTTGAGCTTAAAAAAAAGTATACAT

GACTTTAATGAGGAAAATAAAAATGAATATTGAAATGTT.
```

In some embodiments, a first cell surface antigen and/or a second cell surface antigen is CD88. As such, in some cases, a specific binding member (e.g., a first specific biding member, a reference antibody, etc.) specifically binds to CD88. In other words, in some cases, a specific binding member specifically binds to at least a portion (i.e., a fragment, an epitope) of CD88.

Figure 8:
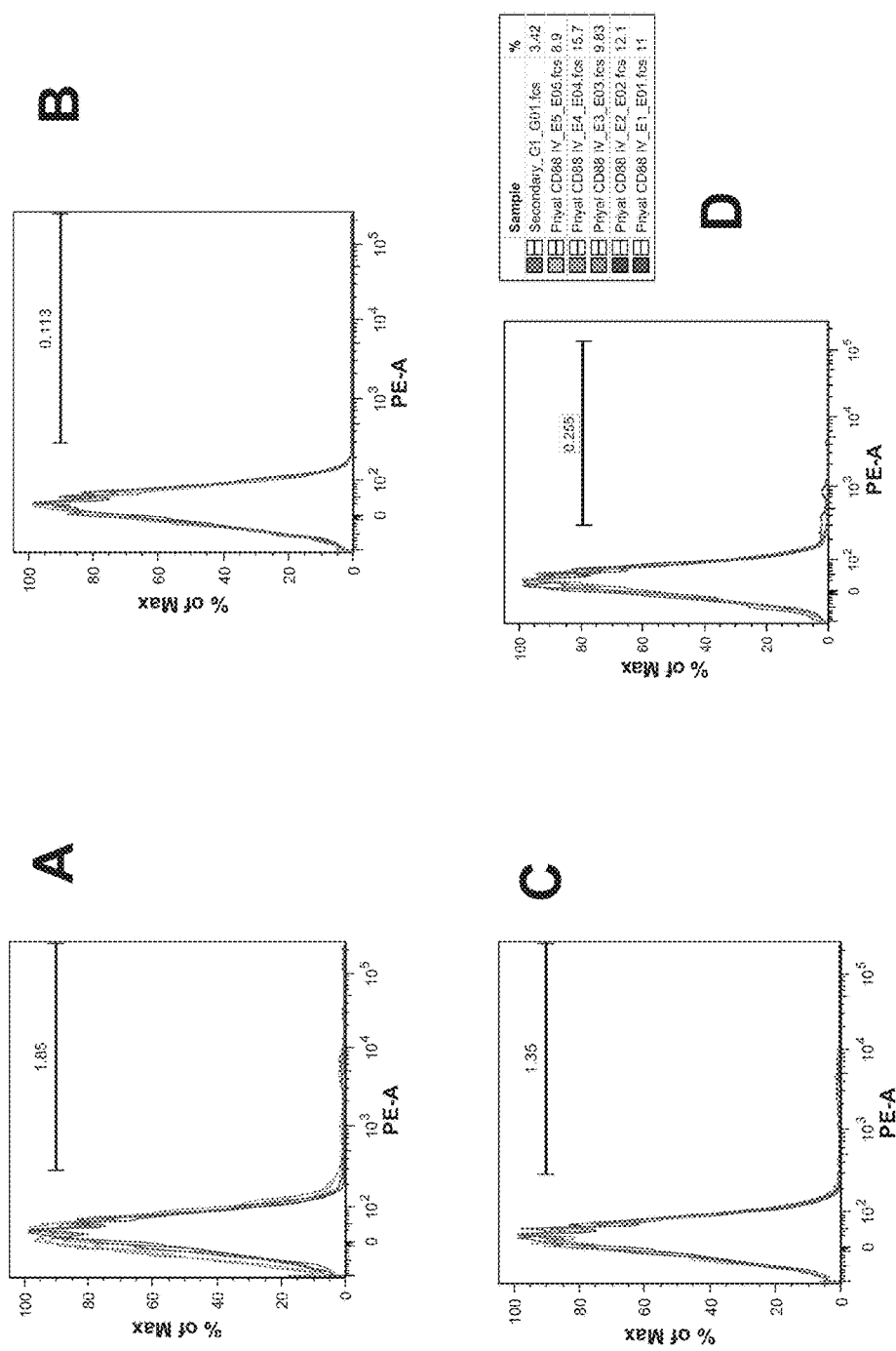
FIG. 8: Confirmation that the mutant antibodies do not bind non-specifically to lymphocytes as a result of the mutational changes made to the antibody binding regions. Two fold serial dilutions of mutant mAbs that were titrated on lymphocytes (A-D) show the absence of non-specific binding to this population of cells.

In some cases, the reference antibody specifically binds CD88; and has the light and heavy chain amino acid sequences that can be readily determined from the amino acid sequence provided in FIGS. 8 and 9.

In some embodiments, the first heavy chain CDR of the blocking reagent can have an amino acid sequence that is 60% or more identical (e.g., 65% or more, 70% or more, 75% or more, 80% or more, 85% or more, 90% or more, 95% or more, 98% or more, 99% or more, 99.5% or more, but less than 100% identical) to a reference sequence. In some embodiments, the second heavy chain CDR of the blocking reagent can have an amino acid sequence that is 60% or more identical (e.g., 65% or more, 70% or more, 75% or more, 80% or more, 85% or more, 90% or more, 95% or more, 98% or more, 99% or more, 99.5% or more, but less than 100% identical) to a reference sequence. In some embodiments, the third heavy chain CDR of the blocking reagent can have an amino acid sequence that is 60% or more identical (e.g., 65% or more, 70% or more, 75% or more, 80% or more, 85% or more, 90% or more, 95% or more, 98% or more, 99% or more, 99.5% or more, but less than 100% identical) to a reference sequence.

In some embodiments, the first light chain CDR of the blocking reagent can have an amino acid sequence that is 60% or more identical (e.g., 65% or more, 70% or more, 75% or more, 80% or more, 85% or more, 90% or more, 95% or more, 98% or more, 99% or more, 99.5% or more, but less than 100% identical) to a reference sequence. In some embodiments, the second light chain CDR of the blocking reagent can have an amino acid sequence that is 60% or more identical (e.g., 65% or more, 70% or more, 75% or more, 80% or more, 85% or more, 90% or more, 95% or more, 98% or more, 99% or more, 99.5% or more, but less than 100% identical) to a reference sequence. In some embodiments, the third light chain CDR of the blocking reagent can have an amino acid sequence that is 60% or more identical (e.g., 65% or more, 70% or more, 75% or more, 80% or more, 85% or more, 90% or more, 95% or more, 98% or more, 99% or more, 99.5% or more, but less than 100% identical) to a reference sequence.

Examples of specific heavy and light chain sequences of interest are provided in FIGS. 10 and 9 (SEQ ID NOs:07 & 04, respectively).

Binding and Affinity

As mentioned above, a subject blocking reagent may be a variant of a reference antibody. In some cases, the reference antibody specifically binds the first cell surface antigen. In some cases, the reference antibody specifically binds to a second cell surface antigen (i.e., a different antigen than the antigen of interest), and the blocking reagent binds with reduced affinity to the second cell surface antigen (reduced affinity relative to the affinity of the reference antibody for the second cell surface antigen), where in some instances the blocking reagent does not specifically bind to the second cell surface antigen.

In some cases, binding affinity can be relative binding affinity. For example, in some cases a blocking reagent binds a cell surface antigen with reduced affinity relative to the affinity with which a reference antibody binds the cell surface antigen. Relative affinity (e.g., the affinity of a blocking reagent for an antigen compared to the affinity of a specific binding member (e.g., an antibody) for the antigen) can be measured using any convenient immune assay (e.g., flow cytometry, radioimmunoassays, enzyme-linked immunosorbent assays (ELISA), Western Blot, assays based on surface plasmon resonance (SPR), Kinetic Exclusion Assay (KinExA), biolayer interferometry (e.g., Octet QKe), and the like). Relative binding can be determined without necessitating the measurement of affinity values.

In some cases, affinity can be measured to obtain a measured value for binding affinity using any convenient assay. For example, binding affinity can be measured using by assays (e.g., label free assays) based on surface plasmon resonance (SPR) (e.g., BIACORE SPR), Kinetic Exclusion Assay (KinExA), biolayer interferometry (e.g., Octet QKe), and the like. Association and dissociation rate constants can also be measured using such assays.

In some embodiments, the affinity of a subject blocking reagent for a cell surface antigen is reduced by 10% or more relative to the affinity of a specific binding member (e.g., a first specific binding member and/or a reference antibody) for the cell surface antigen (e.g., 15% or more, 20% or more, 25% or more, 30% or more, 35% or more, 40% or more, 35% or more, 50% or more, 55% or more, 60% or more, 65% or more, 70% or more, 75% or more, 80% or more, 85% or more, 90% or more, 95% or more, or 98% or more).

In other words, in some embodiments, the affinity a subject blocking reagent for a cell surface antigen is 90% or less the affinity of a specific binding member (e.g., a first specific binding member and/or a reference antibody) for the cell surface antigen (e.g., 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 2% or less).

As mentioned above, a subject blocking reagent is a variant of a reference antibody, where the reference antibody specifically binds a second cell surface antigen (a cell surface antigen that is different than the target antigen, i.e., different than the antigen specifically bound by the first specific binding member). In some cases, a subject blocking reagent binds to the surface of a cell but: (i) does not specifically bind the second cell surface antigen; or (ii) binds the second cell surface antigen with reduced affinity (reduced affinity compared to the affinity with which the reference antibody binds the second cell surface antigen). In some cases, the binding affinity of the blocking reagent for the second cell surface antigen is 10% or more reduced (e.g., 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or 98% or more) compared to the affinity with which the reference antibody binds the second cell surface antigen.

As mentioned above, in some cases, a subject blocking reagent is a variant of an anti-CD88 antibody (a reference antibody that specifically binds CD88). In some cases, a subject blocking reagent does not specifically bind to CD88. In some cases, a subject blocking reagent binds to CD88 with a reduced affinity compared to the affinity with which a reference antibody (e.g., an anti-CD88 antibody) binds to CD88. In some cases, the binding affinity of the blocking reagent for CD88 is 10% or more reduced (e.g., 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or 98% or more) compared to the binding affinity of a reference antibody (e.g., an anti-CD88 antibody) for CD88.

In some embodiments, a subject blocking reagent does not specifically bind to a specified cell surface antigen (e.g., a cell surface antigen that is specifically bound by a first specific biding member, a cell surface antigen that is specifically bound by a reference antibody, etc.). In some embodiments, a subject blocking reagent does not detectably bind to a specified cell surface antigen (e.g., a cell surface antigen that is specifically bound by a first specific biding member, a cell surface antigen that is specifically bound by a reference antibody, etc.).

Blocking compositions may include a blocking reagent, e.g., as described above, present in a suitable medium, such as a liquid medium, e.g., an aqueous medium. Where the blocking composition is a liquid, the concentration of the blocking reagent in the liquid medium may vary. Blocking composition may include only the blocking reagent and a solvent, e.g., water, or may include one or more additional components, e.g., buffering agents, preservatives, etc., as desired.

Methods for Preparing a Blocking Reagent

A blocking reagent as described herein can be prepared by recombinant expression of light and heavy chain genes in a host cell. To express a blocking reagent, a host cell is transfected with one or more recombinant expression vectors having nucleic acid sequences encoding the light and heavy chain variable regions of the blocking reagent such that at least the light and heavy chain variable regions are expressed in the host cell (e.g., any convenient cell that can be used to secret antibodies into the culture medium) and secreted into the medium. The blocking reagent can be recovered from the culture medium. Standard recombinant nucleic acid (DNA) methodologies can be used to obtain nucleic acids having sequences encoding the heavy and light chain variable regions, incorporate these nucleic acids into recombinant expressions vectors, and introduce the vectors into host cells (e.g., CHO cells, NSO myeloma cells, COS cells, HEK-293 cells, SP2 cells, E. coli, and the like), such as those described in Sambrook, Fritsch and Maniatis (eds), Molecular Cloning: A Laboratory Manual, Second Edition, Cold Spring Harbor, New Your, (1989), Ausubel, F. M. et al. (eds.) Current Protocols in Molecular Biology, Greene Publishing Associates (1989) and in U.S. Pat. No. 4,816,397 by Boss et al.

Nucleic Acids and Genetically Modified Cells

Aspects of the disclosure include nucleic acids encoding a subject blocking reagent. A subject nucleic acid includes a first nucleotide sequence that encodes at least one of: (i) a heavy chain variable region comprising 3 heavy chain complementarity determining regions (CDRs) of a blocking reagent; and (ii) a light chain variable region comprising 3 light chain complementarity determining regions (CDRs) of a blocking reagent. In some cases, the nucleic acid is an expression vector in which the nucleotide sequence encoding the blocking reagent is operably linked to a promoter.

Aspects of the disclosure also include genetically modified cells. In some cases, the genetically modified cell has an expression vector having a nucleotide sequence that encodes the heavy chain variable region of a subject blocking reagent. In some cases, the genetically modified cell has an expression vector having a nucleotide sequence that encodes the light chain variable region of a subject blocking reagent. In some cases, the genetically modified cell has two expression vectors, one encoding the heavy chain variable region of a subject blocking reagent, and the other encoding the light chain variable region of the blocking reagent. In some cases, the genetically modified cell has an expression vector having both (i) a nucleotide sequence that encodes the heavy chain variable region of a subject blocking reagent, and (ii) a nucleotide sequence that encodes the heavy chain variable region of the blocking reagent.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. The transforming DNA may be maintained on an episomal element such as a plasmid. A stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA.

Suitable methods of genetic modification (also referred to as "transformation") include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. The choice of method of genetic modification is generally dependent on the type of cell being transformed and the circumstances under which the transformation is taking place (e.g., in vitro, ex vivo, or in vivo).

Methods of Synthesizing Blocking Reagents from a Reference Antibody

Aspects of the disclosure include methods of producing a cell surface blocking reagent. Aspects of embodiments of the methods include: (a) generating a variant of a reference antibody, (b) assaying the variant antibody to determine whether the variant antibody binds to the cell surface antigen with reduced affinity relative to the affinity with which the reference antibody binds to the cell surface antigen, and (c) determining that the variant antibody is a cell surface blocking reagent when the variant antibody binds to the cell surface antigen with reduced affinity relative to the affinity with which the reference antibody binds to the cell surface antigen.

The step of generating a variant of a reference antibody generally includes introducing at least one mutation in the nucleotide sequence encoding at least one CDR of the reference antibody. Any convenient method can be used to introduce mutations (such as deletions, additions, and/or substitutions) in the nucleic acid molecule encoding a reference antibody, including, for example, site-directed mutagenesis and PCR-mediated mutagenesis. In one aspect, the derivatives include 10 or less amino acid substitutions, 9 or less amino acid substitutions, 8 or less amino acid substitutions, 7 or less amino acid substitutions, 6 or less amino acid substitutions, 5 or less amino acid substitutions, 4 or less amino acid substitutions, 3 or less amino acid substitutions, 2 or less amino acid substitutions, or 1 amino acid substitution relative to the reference antibody. Another method is to generate the whole gene de novo via gene synthesis in its nearly identical but mutated form and put it into a suitable expression vector. Protein expression can be carried out by any suitable means, e.g., mammalian cell expression, *E. coli*, Baculovirus Plant expression etc., such as described in greater detail above.

Mutations can be introduced randomly along all or part of the coding sequence, such as by saturation mutagenesis, and the resultant mutants can be screened. Following mutagenesis, the encoded variant antibodies can be expressed and the binding affinity (e.g., relative or absolute) of the variant antibodies for the cell surface antigen can be measured and compared to the binding affinity of the reference antibody for the cell surface antigen.

The step of assaying the affinity of the variant antibody for the cell surface antigen, with respect to measuring affinity (e.g., relative affinity), can include measuring the affinity to obtain an affinity value (e.g., using label free assays based on surface plasmon resonance (SPR) (e.g., BIACORE SPR), kinetic exclusion assay (KinExA), biolayer interferometry (e.g., Octet QKe), and the like), and/or measuring a relative affinity (e.g., using any convenient immunoassay method, e.g., ELISA, flow cytometry, Western blot, etc.).

In some embodiments, the method further includes determining the amino acid sequence of at least one CDR of the variant antibody. In some cases, a nucleic acid encoding the variant antibody (one, for example, that has been shown to have a reduced affinity for the antigen), or at least the portion of the nucleic acid encoding the at least one CDR, is sequenced.

Methods of Using Blocking Compositions

Aspects of the disclosure include methods of using blocking compositions, e.g., as described above, such as methods of labeling a cell. In some embodiments, the methods include contacting a cell with (i) a first specific binding member that specifically binds to a first cell surface antigen, and (ii) a blocking composition including a blocking reagent that no longer binds to the surface of a cell via the first cell surface antigen. The methods may further include detecting the presence or absence of the first antibody on the cell. In some embodiments, the blocking reagent binds to the first cell surface antigen with a reduced affinity or no measurable affinity compared to the affinity with which the first specific binding member binds to the first cell surface antigen, e.g., as described above.

As mentioned above, a blocking reagent (e.g. unlabeled) binds to secondary antigens (e.g., "sticky" antigens) in order to block a first specific binding member from binding the secondary antigens, thereby reducing background signal measured when detecting the first specific binding member. In some instances, the first specific binding member includes a label moiety. A "label moiety" is any moiety that provides for signal detection and may vary widely depending on the particular nature of the assay. Label moieties of interest include both directly (e.g., a fluorescent label) and indirectly (e.g., a binding pair member) detectable labels. Suitable detectable (directly or indirectly) label moieties for use in the methods include any moiety that is detectable by spectroscopic, photochemical, biochemical, immunochemical, electrical, optical, chemical, or other means. For example, suitable labels include biotin for staining with labeled streptavidin conjugate; a fluorescent dye (e.g., fluorescein, Texas red, rhodamine, ALEXAFLUOR® labels, and the like); a radiolabel (e.g., $^{3}H$, $^{125}I$, $^{35}S$, $^{14}C$, or $^{32}P$); an enzyme (e.g., peroxidase, alkaline phosphatase, galactosidase, and others commonly used in an ELISA); a fluorescent protein (e.g., green fluorescent protein, red fluorescent protein, yellow fluorescent protein, and any convenient derivatives thereof); a metal label; a colorimetric label; a binding pair member; and the like. Any binding pair member can be suitable for use as an indirectly detectable label moiety A given blocking reagent can be unlabeled, or can be labeled with a label moiety that is distinguishable from label moiety of the first specific binding member. In some embodiments, the cell is contacted with the blocking reagent prior to being contacted with the first specific binding member. In some embodiments, the cell is contacted with the blocking reagent and the first specific binding member at the same time.

The step of detecting the presence or absence of the first specific binding member can be performed using any convenient method for detecting the presence or absence of the first specific binding member (e.g., antibody) on the cell. Suitable methods of detecting include, but are not limited to: flow cytometry (e.g., Fluorescence Activated Cell Sorting (FACS)); Western blot; ELISA imaging, immunohistochemistry; and the like.

Flow cytometry is a well-known methodology using multi-parameter data for identifying and distinguishing between different particle types (i.e., particles, such as cells, that vary from one another in terms of label wavelength, label intensity, size, etc.) in a fluid medium. In performing flow cytometry (i.e., flow cytometrically analyzing particles (e.g., cells) of a sample), a liquid sample (containing particles to be analyzed) is first introduced into a sample loading region, which is sometimes referred as a sample injection chamber, of a flow cytometer. During sample acquisition, the chamber of the sample loading region is pressurized to force sample into the flow path of the flow cytometer, toward the particle interrogation region.

When in the flow path, particles are passed substantially one at a time through the particle interrogation region, where each of the particles is exposed individually to an energy source (e.g., a light source) and measurements of light scatter parameters (e.g., forward scatter, side scatter, etc.) and/or fluorescent emissions as desired (e.g., one or more fluorescent emissions) are separately recorded for each particle. The energy source may include an illuminator that emits light of a single wavelength, such as that provided by a laser (e.g., He/Ne or argon) or a mercury arc lamp with appropriate filters. Examples of excitation light sources include lasers, light emitting diodes, and arc lamps. For example, light at 488 nm may be used as a wavelength of emission in a flow cytometer having a single sensing region. For flow cytometers that emit light at two or more distinct wavelengths, additional wavelengths of emission light may be employed, where specific wavelengths of interest typically include, but are not limited to: 535 nm, 635 nm, and the like. A subject flow cytometer can have one or more lasers (e.g., two or more, three or more, four or more, five or more, six or more, etc.).

In the particle interrogation region, detectors (e.g., light collectors, such as photomultiplier tubes (or "PMT")), are used to record light that passes through each particle (generally referred to as forward light scatter), light that is reflected orthogonal to the direction of the flow of the particles through the sensing region (generally referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions (FL1, FL2, etc.) comprise a separate parameter for each particle (or each "event"). Thus, for example, two, three or four parameters can be collected (and recorded) from a particle labeled with two different fluorescence markers.

The data recorded for each particle is analyzed in real time and/or stored in a data storage and analysis device, such as a computer, as desired. Publications from the scientific and patent literature describing various designs, configurations, and uses of flow cytometers include, for example: (i) Jaye et al., J Immunol. 2012 May 15; 188(10):4715-9: Translational applications of flow cytometry in clinical practice; (ii) Krutzik et al., Curr Protoc Cytom. 2011 January; Chapter 6: Unit 6.31: Fluorescent cell barcoding for multiplex flow cytometry; (iii) Black et al., Assay Drug Dev Technol. 2011 February; 9(1):13-20: Cell-based screening using high-throughput flow cytometryl (iv) Abayomi et al., Cytometry B Clin Cytom. 2008; 74 Suppl 1:S80-9: Flow cytometry as the spearhead for delivering sustainable and versatile laboratory services to HIV-burdened health care systems of the developing world: a Caribbean model; (v) Snow et al., Cytometry A. 2004 February; 57(2):63-9: Flow cytometer electronics; (vi) Schmid et al., Cytometry A. 2003 December; 56(2):113-9: Biosafety concerns for shared flow cytometry core facilities; and (vii) U.S. Pat. Nos. 8,502,976, 8,486,371, 8,441,637, 8,441,624, 7,990,525, 8,021,872, 7,611,849, and 7,354,773; all of which citations are hereby incorporated by reference in their entirety.

Thus, flow cytometry can be used to detect the presence or absence of the first specific binding member on the surface of a cell, and such detection is enhanced (e.g., signal to noise is increased) when the cell is also contacted with a subject blocking reagent.

Because a subject blocking reagent binds to the cell surface, a subject blocking reagent can be used in conjunction with any specific binding member that specifically binds to any cell surface antigen of interest. In some cases, the species from which the first specific binding member (e.g., an antibody that specifically binds the cell surface antigen of interest) is derived is the same species from which the subject blocking reagent is derived. For example, in some cases, the first specific binding member is a rabbit polyclonal antibody that specifically binds a cell surface antigen of interest and the blocking reagent is an antibody or binding fragment thereof derived from a rabbit (i.e., the non-CDR portions of the blocking reagent have rabbit-derived amino acid sequences).

A subject blocking reagent can be used in conjunction with a first specific binding member to detect an antigen on any cell of interest, as long as the cell has expresses the antigen of interest. Thus, which cell is appropriate will depend on the nature of the first specific binding member (i.e., will depend on what antigen the first specific binding member specifically binds). A "cell" or "target cell" as used herein refers to any desired cell. A subject cell can be of any mammalian species (e.g., human, non-human primate, rat, mouse, pig, sheep, cow, rabbit, camel, etc.), of any cell type (neural, hepatic, hematopoietic, etc.), of any cell line (CHO, HEK293, COS, etc.), etc. In order to detect the presence of a first cell surface antigen on the cell, the cell must have the antigen on the cell surface.

A target cell can be a cell in a biological sample and/or a cell isolated from/extracted from a biological sample. A "biological sample" encompasses a variety of sample types obtained from an organism (or obtained in vitro, e.g., via cell culture) (e.g., in some cases substantially in liquid form) and includes cells of the organism. The definition encompasses blood, blood-derived samples, and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, enrichment for certain components, or labeling (e.g., labeling with a label). The term "biological sample" encompasses a clinical sample, and also includes cells in culture, cell supernatants, cell lysates, serum, plasma, cerebrospinal fluid, urine, saliva, biological fluid, and tissue samples. Any convenient method for preparing a biological sample (e.g., a biopsy) for use in a cell labeling method can be used. When performing flow cytometry, particles contained in the biological sample are generally separated from one another to allow for flow through the flow path of a flow cytometer.

Flow Cytometry Systems

Aspects of the present disclosure include flow cytometer systems, where the systems include a sample which includes a blocking reagent, e.g., as described (for sample, the systems include a sample to be analyzed that has been prepared by contacting an initial sample with (i) a first specific binding member that specifically binds to a first cell surface antigen; and (ii) a blocking reagent, e.g., as described above). Flow cytometers of interest include, but are not limited, to those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference. In some instances, the flow cytometer includes: a flow channel; at least a first light source configured to direct light to an assay region of the flow channel (where in some instances the cytometer includes two or more light sources); a first detector configured to receive light of a first wavelength from the assay region of the flow channel; and a second detector configured to receive light of a second wavelength from the assay region of the flow channel. A flow cytometer system in accordance with embodiments of the invention may include a flow cytometer (having a sample loading region and a flow path, etc., as described above) and a cell-containing biological sample in the sample loading region, where the biological sample is contacted with: (i) a first specific binding member that specifically binds to a first cell surface antigen; and (iii) a subject blocking reagent. The sample that includes the blocking reagent may be present in a variety of locations in a flow cytometer, e.g., a sample loading region, an analysis region, e.g., cuvette, etc.

Kits

Aspects of the disclosure further include kits (e.g., a blocking kit) for practicing the subject methods. A subject kit includes a subject blocking reagent and a container, e.g., for use of rabbit polyclonal antibody for immunohistochemical staining or flow cytometry with or without additional monoclonal antibodies. Any convenient container (glass vial, plastic vial, screw-top tube, and the like) can be used and can be made out of any convenient material (e.g., glass, plastic, etc). In some embodiments, kits may further include a first specific binding member (e.g., an antibody of interest), a diluent, a buffer, salts, enzymes, enzyme co-factors, substrates, detection reagents, label moieties, and the like.

Components of the kits may be present in separate containers, or multiple components may be present in a single container. For example, a blocking reagent and an antibody of interest (a first specific binding member) may be present in different containers, or combined in a single container, as desired. In some instances, the container(s) are sterile packaging containers.

In addition to the above-mentioned components, a subject kit may further include instructions for using the components of the kit, e.g., to practice the subject methods. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., portable flash drive, CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Figure 2:
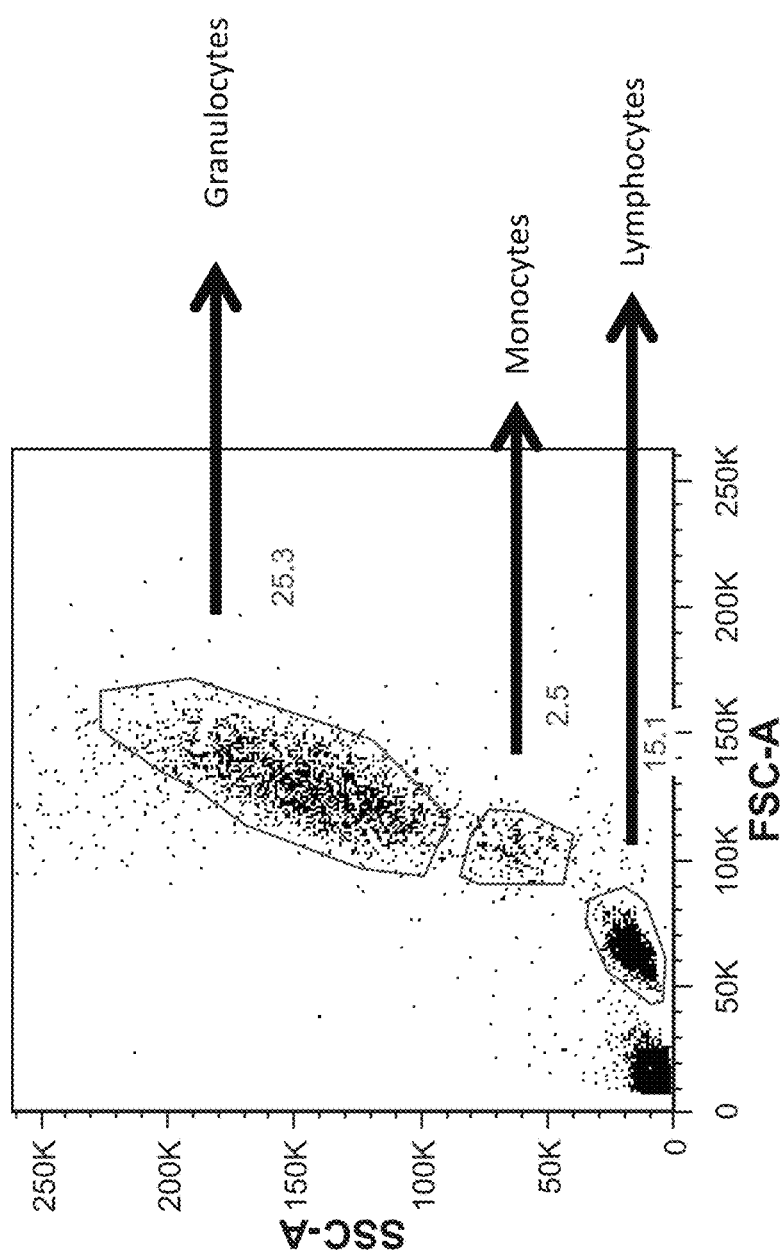
FIG. 2 provides a representative flow cytometry analysis of lysed human whole blood and populations of cells.
Figure 3:
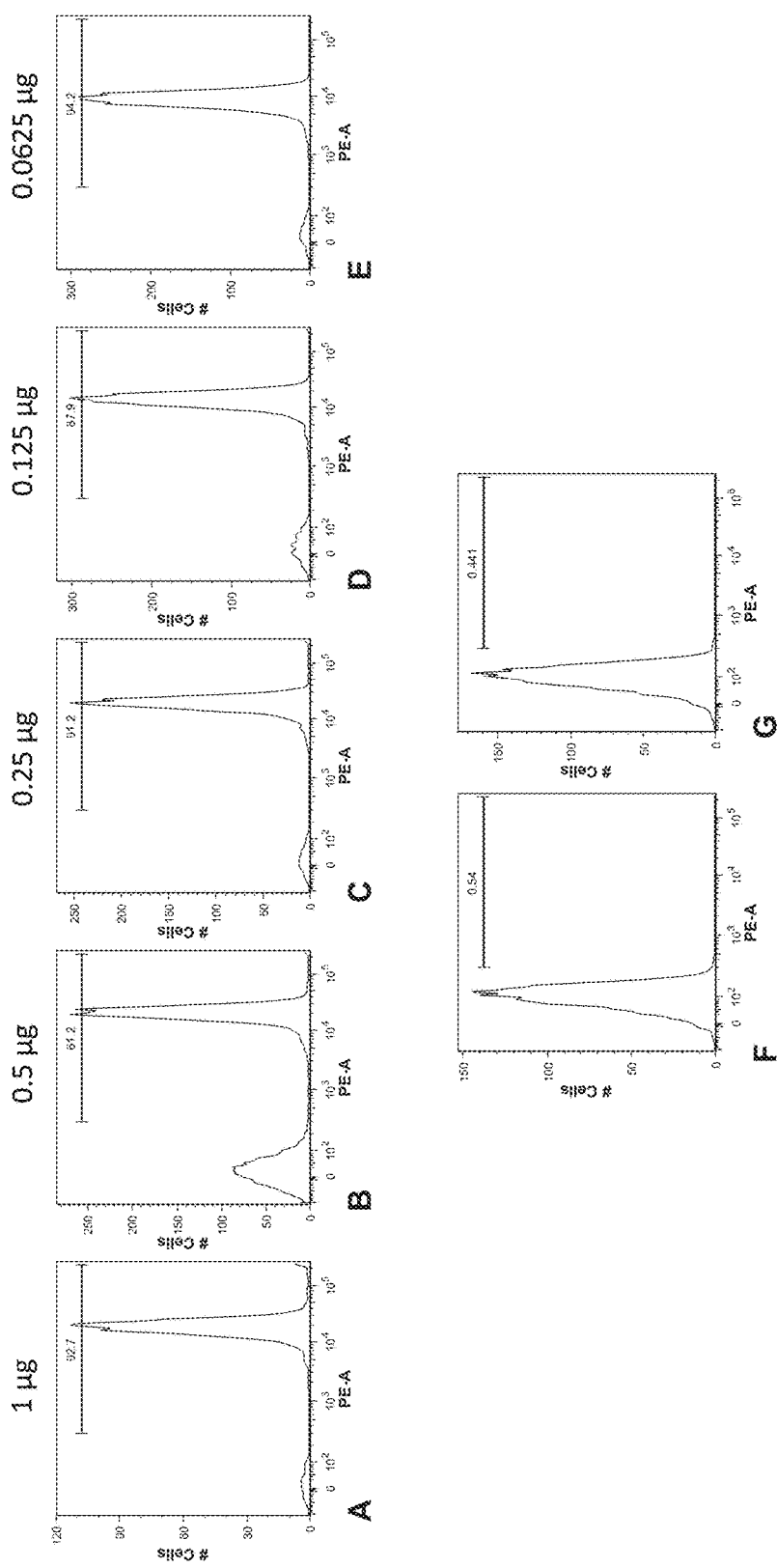
FIG. 3 depicts results from flow cytometry assays. (A-E) Titration of different amounts of a representative anti-human CD88 parental reference monoclonal antibody to the native CD88 antigen expressed on granulocytes; (F) Negative control: non-specific binding of secondary anti-rabbit phycoerythrin (PE) conjugated antibody on cells alone (primary antibody absent). (G) Negative control: background autofluorescence of unstained cells.
Figure 11:
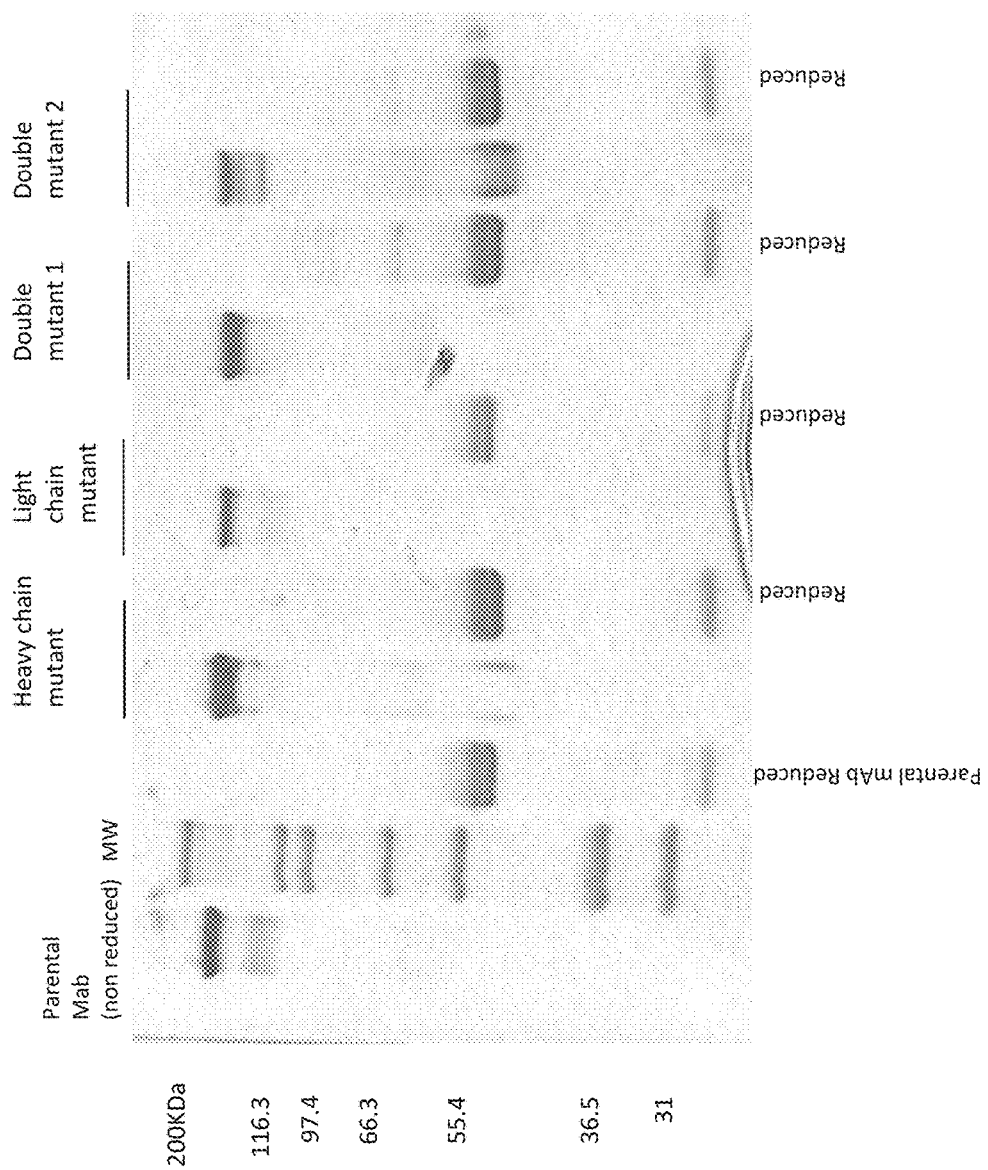

To improve the specificity of staining of a rabbit polyclonal antibody (e.g., for flow cytometry), a subject recombinant blocking reagent was produced according to the protocol summarized in FIG. 1. In vitro mutagenesis was carried out focusing on the complementary determining regions (CDRs) of the variable region genes encoding the heavy chain and the light chain of the rabbit anti human CD88 mAb. The mutagenesis was empirically focused on codons encoding key chemical group amino acids commonly found in variable regions to be contact residues.

mRNA encoding the heavy and light chains (CDRs 1-3) of the rabbit anti-human CD88 mAb was isolated from hybridoma cells (hybridoma cell line CD88 clone C85-4124), and was reverse transcribed. The PCR product was sequenced to confirm the sequence of the reference antibody Hc and Lc. In vitro site-directed mutagenesis was performed using the QuikChange II XL Site-Directed Mutagenesis Kit (Catalog #200521, Agilent) to generate variant Hc and Lc that differed from the parental/reference chains by anywhere from 1 to up to 7 amino acid substitutions. Thermal cycling was performed with Dpn I digestion of template. Transformation was carried out in XL 10-Gold Ultra-competent cells (Agilent) in an incubator at 37° C. Single cell colonies were chosen and grown in a shaker overnight at 250 rpm and 37° C. These mutations were made within the boxed sequences indicated in FIGS. 9 and 10. Variant polynucleotides were cloned into plasmids (BD3115, BD3114, BD3113), which were transformed subsequently into E. coli. Cloned plasmid DNA was extracted and the specific mutations of the CD88 heavy and light chains were confirmed by sequencing (FIGS. 9 and 10; FIG. 9 mutations: Y51A, FIG. 10 mutations: R116A in the heavy chain CDR). Following sequencing, protein expression was carried out by transient transfection of 293F mammalian cells (LifeTechnologies) with the mutated DNA molecules. The supernatants of transfected cells were harvested after one week (168 hours) and the secreted mAbs were purified using protein G affinity chromatography. Protein expression was confirmed via SDS-PAGE (FIG. 11) and the reduced binding affinity of the mutant (i.e., variant) antibodies to the CD88 antigen was tested in ELISA and flow cytometry assays (FIGS. 4 to 8), relative to that of the parental CD88 monoclonal reference antibody (FIG. 3). The gating strategy for a typical flow cytometry experiment is shown in FIG. 2 performed on whole human lysed blood.

A. ELISA/Flow Cytometry

Reactivity of the variant mAbs against recombinant CD88 proteins (Rabbit monoclonal antibody) produced in 293F cells was determined by enzyme-linked immunoabsorbent assay (ELISA). 96-well plates were blocked overnight at 4° C. with a relevant and irrelevant control peptide. The next day, plates were washed and incubated with ELISPOT blocking buffer and primary antibody for one hour. After that, secondary antibody (BD Pharmingen HRP Goat Anti-Rabbit Ig (Cat No 554021)) was added for one hour. Plates were washed again and substrate was added. A signal by change in color was detected and the O.D. values were measured in the spectrophotometer at 405 nm.

B. Flow Cytometry

For cell surface staining with the parental rabbit anti-human CD88 mAb, PBMCs in PBS containing 2% BSA were mixed with parental rabbit anti-human CD88 mAbs at concentrations of 1 µg, 0.5 µg, 0.25 µg, 0.125 µg and 0.0625 µg as shown in FIG. 3 (A-E) and incubated for 1 hr at 4° C. The cells were washed with PBS containing 2% BSA and incubated at 4° C. for 30 minutes with BD Pharmingen PE Goat Anti-rabbit IgG (Cat No 558146). The cells were washed with PBS containing 2% BSA, and analyzed with a BD FACS Canto II Flow cytometer. Non-specific binding of the secondary anti-rabbit PE-conjugated antibody on the cells alone (primary antibody absent; FIG. 3F) and background autofluorescence by unstained cells (secondary antibody absent; FIG. 3G) served as negative controls for the assay. The % positive signal was detected.

Figure 4:
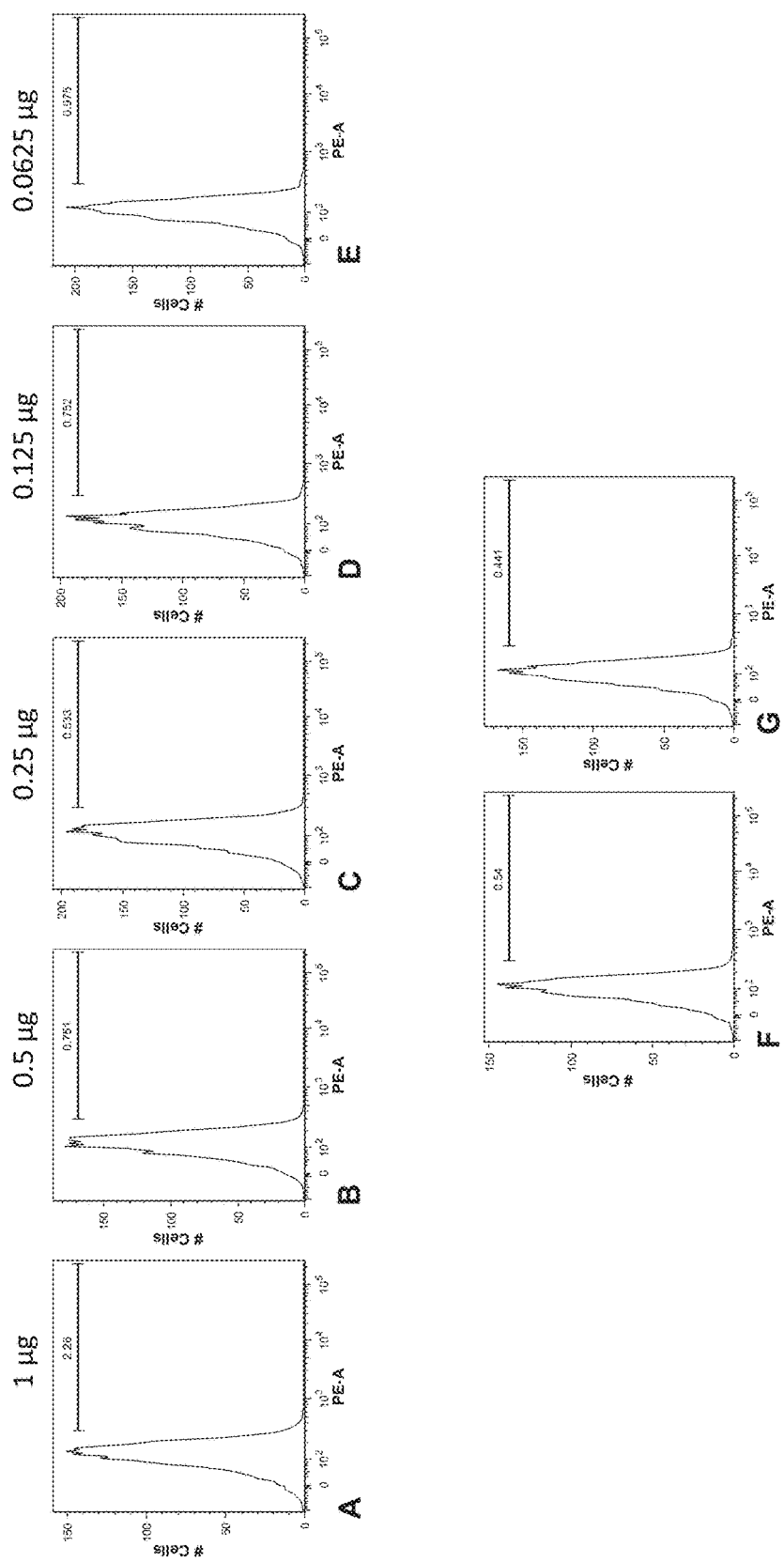
FIG. 4: Titration of a mutant recombinant mAb which lacks binding to CD88 (A-E). This particular antibody has a mutation (R116A) in the heavy chain binding region which removed binding specificity. (F) Negative control: non-specific binding of secondary anti rabbit phycoerythrin (PE) conjugated antibody on the granulocytes alone (primary antibody absent). (G) Negative control: background autofluorescence of unstained cells.
Figure 5:
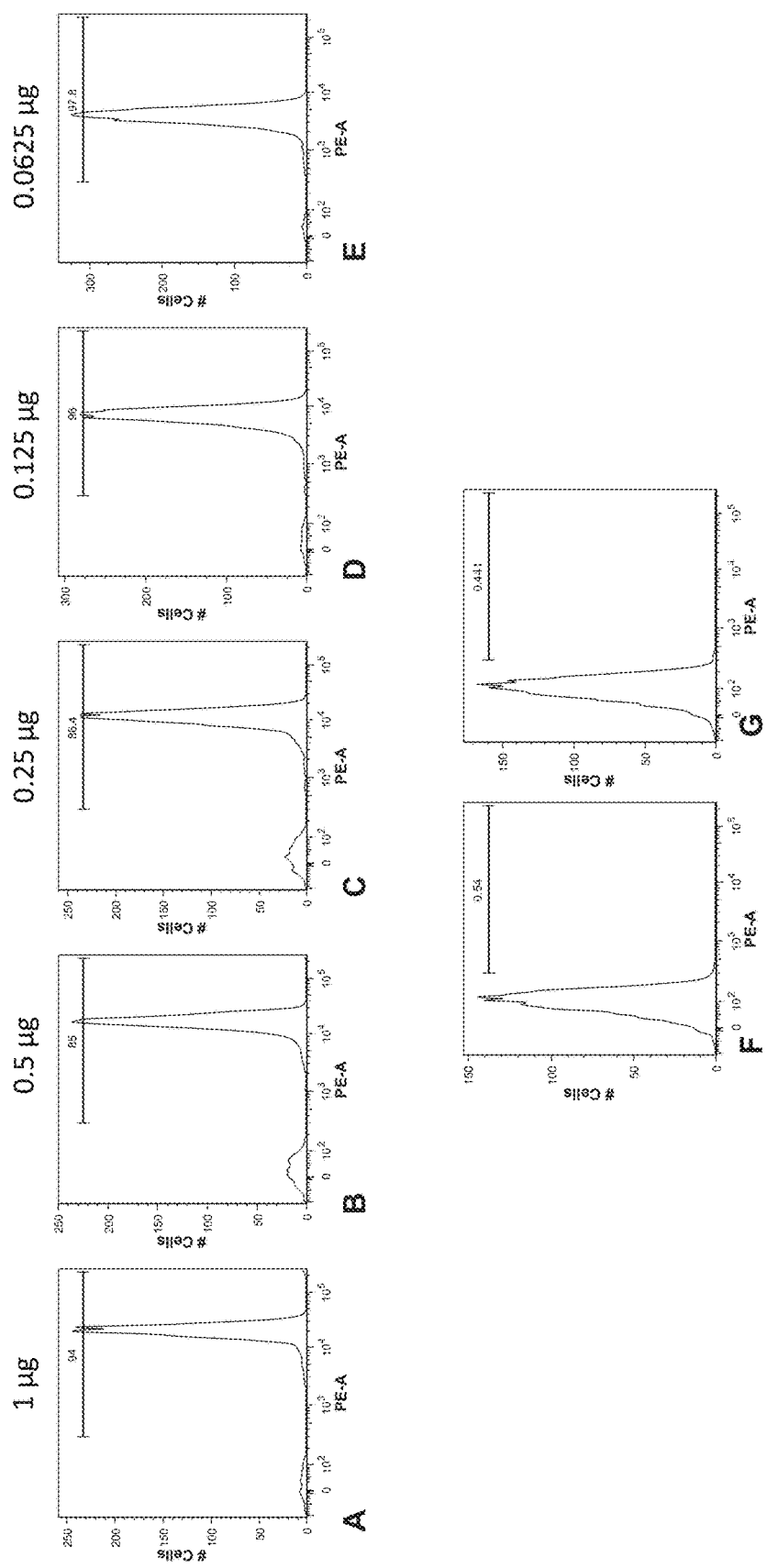
FIG. 5: Titration of a mutant recombinant mAb which has negligible binding to CD88 (A-E) This particular antibody has a mutation in the light chain binding region (Y51A) which removed binding specificity. (F) Negative control: non-specific binding of secondary anti rabbit PE-conjugated antibody on the granulocytes alone (primary antibody absent). (G) Negative control: background autofluorescence of unstained granulocytes.
Figure 6:
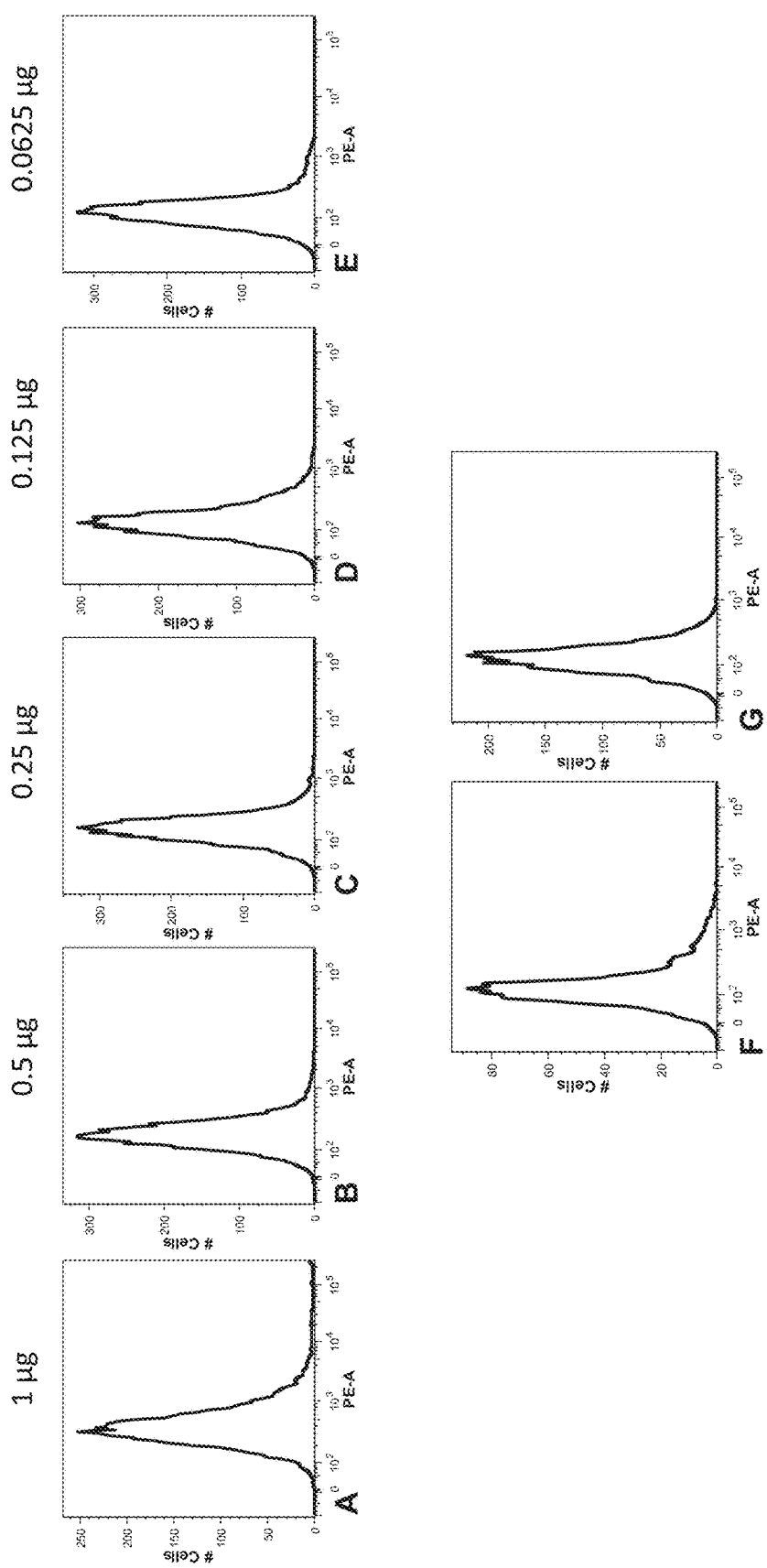
FIG. 6: Titration of a mutant recombinant mAb which has removed binding to CD88 (A-E). This particular antibody has a mutation in both the heavy chain and light binding region which removed binding specificity (R116A in the heavy chain CDR and Y51A). (F) Negative control: non-specific binding of secondary anti rabbit PE-conjugated antibody on the granulocytes alone (primary antibody absent). (G) Negative control: background autofluorescence of unstained granulocytes.
Figure 7:
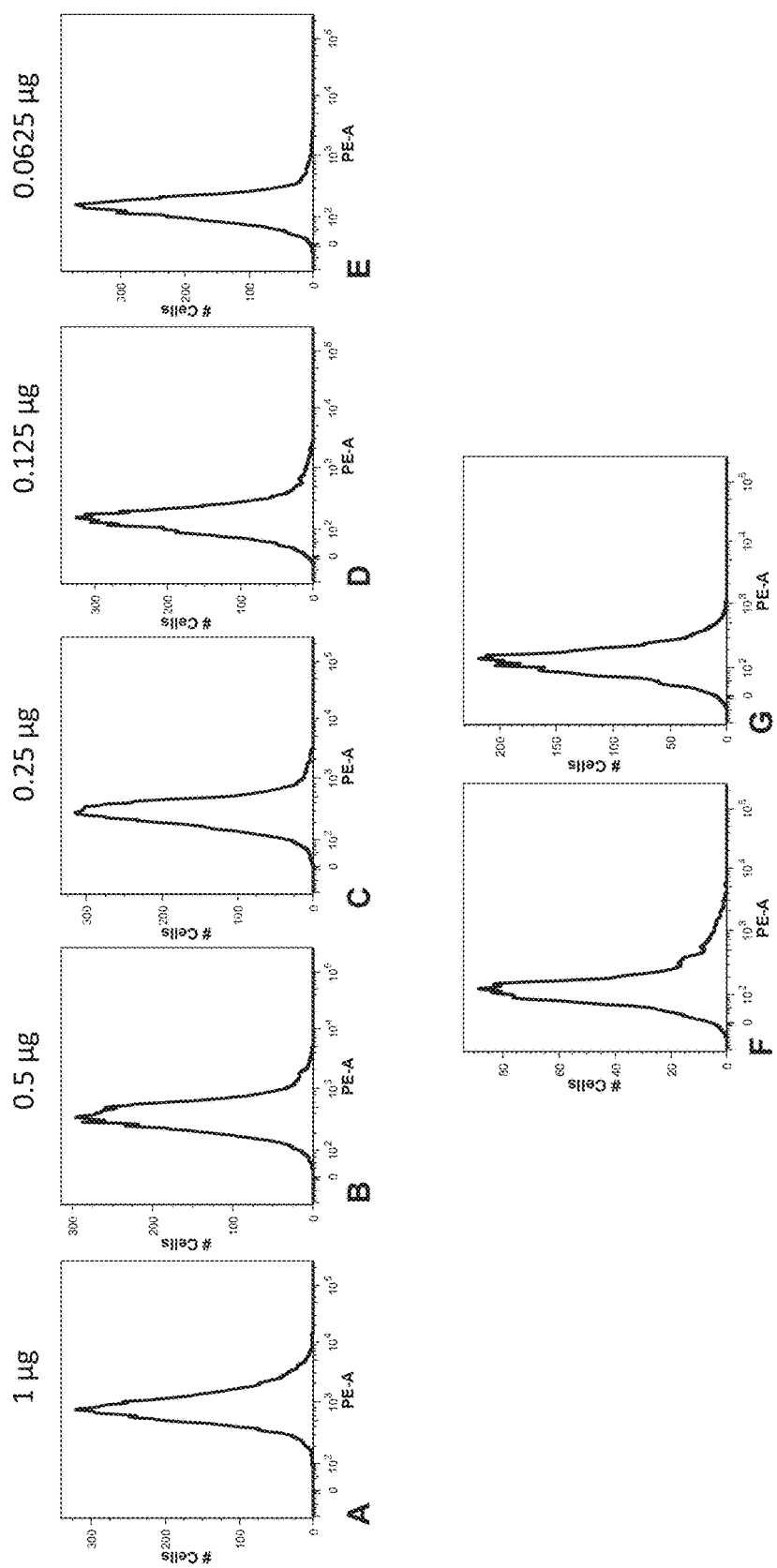
FIG. 7: Titration of a mutant recombinant mAb which has removed binding to CD88 (A-E). This particular antibody is another double mutant that has mutation in both the heavy chain and light binding region which removed binding specificity (R116A in the heavy chain CDR and Y51F). (F) Negative control: non-specific binding of secondary anti rabbit PE-conjugated antibody on the cells alone (primary antibody absent). (G) Negative control: background autofluorescence by unstained cells.

The binding of the variant rabbit anti-human CD88 mAbs was assayed as for the parental mAb, and the results for four variants are shown in FIGS. 4-7. FIG. 4 (A-E) shows the binding at concentrations of 1 µg, 0.5 µg, 0.25 µg, 0.125 µg and 0.0625 µg of a first variant having a single amino acid substitution R116A in the heavy chain CDR. Panels F and G show fluorescence of the negative controls as described for the parental mAb. FIG. 5 (A-E) shows the binding at concentrations of 1 ug, 0.5 ug, 0.25 ug, 0.125 ug and 0.0625 ug of a second variant mAb having a substitution Y51A in the light chain CDR. Panels F and G show fluorescence of the negative controls as described for the parental mAb. FIG. 6 (A-E) shows the binding at concentrations of 1 ug, 0.5 ug, 0.25 ug, 0.125 ug and 0.0625 ug of a third variant mAb having a substitution R116A in the heavy chain and a substitution Y51A in the light chain CDRs. Panels F and G show fluorescence of the negative controls as described for the parental mAb. FIG. 7 (A-E) show the binding at concentrations of 1 ug, 0.5 ug, 0.25 ug, 0.125 ug and 0.0625 ug of a fourth variant mAb having a substitution R116A in the heavy chain and a substitution Y51F in the light chain CDRs. Panels F and G show fluorescence of the negative controls as described for the parental mAb.

To verify that the variant mAbs do not bind non-specifically to lymphocytes, binding of serially diluted variant mAbs (10 µg to 0.625 µg) of each of the variants was measured. FIG. 7 (A-D) show the lack of binding of the respective first, second, third and fourth variant to lymphocytes, sincelymphocytes do not express CD88. As a control, absence of binding was confirmed in the absence of primary antibody.

| Variant No. | Mutation/Domain (Hc CDR #, Lc CDR#) |
|---|---|
| Control | None - parental antibody |
| Variant 1 (FIG. 4) | R116A, CDR-H3 |
| Variant 2 (FIG. 5) | Y51A, CDR-L1 |
| Variant 3 (FIG. 6) | R116A/Y51A |
| Variant 4 (FIG. 7) | R116A/Y51F |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A blocking composition for use with a reference antibody that specifically binds to a CD88 cell surface antigen, the blocking composition comprising:
   a blocking, reagent, wherein the blocking reagent is variant of an anti-CD38 reference antibody or binding fragment thereof, wherein the reference antibody comprises a heavy chain consisting of SEQ ID NO: 7 and a light chain consisting of SEQ ID NO: 4, wherein the variant antibody comprises at least one single amino acid substitution in at least one CDR of the reference antibody, wherein the at least one single amino acid substitution is selected from the group consisting of R116A, Y51A, Y51F, R116A and Y51A and R116A and Y51F; and wherein the blocking reagent does not specifically bind to the CD88 cell surface antigen.

2. The blocking composition according to claim 1, wherein the variant antibody comprises a R116A substitution.

3. The blocking reagent according to claim 1, wherein the variant antibody comprises a Y51A substitution.

4. The blocking reagent according to claim 1, wherein the variant antibody comprises a Y51F substitution.

5. The blocking reagent according to claim 1, wherein the variant antibody comprises R116A and Y51A substitutions.

6. The blocking reagent according to claim 1, wherein the variant antibody comprises R116A and Y51F substitutions.

7. A kit for use in an immunoassay for detecting the presence of a CD88 antigen on a cell comprising:
   (a) the blocking reagent of claim 1; and
   (b) a container for the blocking reagent.

8. The kit according to claim 7, wherein the variant antibody comprises a R116A substitution.

9. The kit according to claim 7, wherein the variant antibody comprises a Y51A substitution.

10. The kit according to claim 7, wherein the variant antibody comprises a Y51F substitution.

11. The kit according to claim 7, wherein the variant antibody comprises R116A and Y51A substitutions.

12. The kit according to claim 7, wherein the variant antibody comprises R116A and Y51F substitutions.

* * * * *

SEQUENCE LISTING

```
<160> NUMBER OF SEQ ID NOS: 8

<210> SEQ ID NO 1
<211> LENGTH: 350
<212> TYPE: PRT
<213> ORGANISM: Homo sapiens

<400> SEQUENCE: 1

Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30

Leu Arg Val Pro Asp Ile Leu Ala Leu Val Ile Phe Ala Val Val Phe
        35                  40                  45

Leu Val Gly Val Leu Gly Asn Ala Leu Val Val Trp Val Thr Ala Phe
    50                  55                  60

Glu Ala Lys Arg Thr Ile Asn Ala Ile Trp Phe Leu Asn Leu Ala Val
65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
            100                 105                 110
```

```
Pro Ser Leu Ile Leu Leu Asn Met Tyr Ala Ser Ile Leu Leu Leu Ala
        115                 120                 125

Thr Ile Ser Ala Asp Arg Phe Leu Leu Val Phe Lys Pro Ile Trp Cys
    130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
            165                 170                 175

Val Arg Glu Glu Tyr Phe Pro Pro Lys Val Leu Cys Gly Val Asp Tyr
        180                 185                 190

Ser His Asp Lys Arg Arg Glu Arg Ala Val Ala Ile Val Arg Leu Val
        195                 200                 205

Leu Gly Phe Leu Trp Pro Leu Leu Thr Leu Thr Ile Cys Tyr Thr Phe
    210                 215                 220

Ile Leu Leu Arg Thr Trp Ser Arg Arg Ala Thr Arg Ser Thr Lys Thr
225                 230                 235                 240

Leu Lys Val Val Val Ala Val Val Ala Ser Phe Ile Phe Trp Leu
            245                 250                 255

Pro Tyr Gln Val Thr Gly Ile Met Met Ser Phe Leu Glu Pro Ser Ser
        260                 265                 270

Pro Thr Phe Leu Leu Leu Asn Lys Leu Asp Ser Leu Cys Val Ser Phe
    275                 280                 285

Ala Tyr Ile Asn Cys Cys Ile Asn Pro Ile Ile Tyr Val Val Ala Gly
        290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
            325                 330                 335

Arg Ser Thr Val Asp Thr Met Ala Gln Lys Thr Gln Ala Val
        340                 345                 350

<210> SEQ ID NO 2
<211> LENGTH: 2342
<212> TYPE: DNA
<213> ORGANISM: Homo sapiens

<400> SEQUENCE: 2
cttgggcagg agggaccttc gatcctcggg gagcccagga gaccagaaca tgaactcctt      60
caattatacc accctgatt atgggcacta tgatgacaag gatacccctgg acctcaacac     120 ccctgtggat aaaacttcta acacgctgcg tgttccagac atcctggcct tggtcatctt     180
tgcagtcgtc ttcctggtgg gagtgctggg caatgccctg gtggtctggg tgacggcatt     240
cgaggccaag cggaccatca tgccatctg gttcctcaac ttggcggtag ccgacttcct     300
ctcctgcctg gcgctgccca tcttgttcac gtccattgta cagcatcacc actggccctt     360
tggcggggcc gcctgcagca tcctgccctc cctcatcctg ctcaacatgt acgccagcat     420
cctgctcctg gccaccatca gcgccgaccg ctttctgctg gtgtttaaac ccatctggtg     480
ccagaacttc gaggggccg gcttggcctg atcgcctgt gccgtggctt ggggtttagc      540
cctgctgctg accataccct ccttcctgta ccgggtggtc cgggaggagt actttccacc     600
aaaggtgttg tgtggcgtgg actacagcca cgacaaacgg cgggagcgag ccgtggccat     660
cgtccggctg gtcctgggct tcctgtggcc tctactcacg ctcacgattt gttacacttt     720
catcctgctc cggacgtgga gccgcagggc cacgcggtcc accaagacac tcaaggtggt     780
```

-continued

```
ggtggcagtg gtggccagtt tctttatctt ctggttgccc taccaggtga cggggataat      840
gatgtccttc ctggagccat cgtcacccac cttcctgctg ctgaataagc tggactccct      900
gtgtgtctcc tttgcctaca tcaactgctg catcaaccccc atcatctacg tggtggccgg     960
ccagggcttc cagggccgac tgcggaaatc cctcccccagc ctcctccgga acgtgttgac     1020
tgaagagtcc gtggttaggg agagcaagtc attcacgcgc tccacagtgg acactatggc     1080
ccagaagacc caggcagtgt aggcgacagc ctcatgggcc actgtggccc gatgtccccct    1140 tccttcccgg ccattctccc tcttgttttc acttcacttt tcgtgggatg tgttaccttt     1200
agctaactaa ctctcctcca tgttgcctgt ctttcccaga cttgtccctc cttttccagc     1260
gggactcttc tcatccttcc tcatttgcaa ggtgaacact tccttctagg gagcaccctc     1320
ccacccccca ccccccccac acacaccatc tttccatccc aggcttttga aaaacaaaca     1380
gaaacccgtg tatctgggat atttccatat ggcaataggt gtgaacaggg aactcagaat     1440
acagacaagt agaaagattc tcgcttaaaa aaaatgtatt tattttatgg caagttggaa     1500
aatatgtaac tggaatctca aaagttcttt gggacaaaac agaagtccat ggagttatct     1560
aagctcttgt aagtgagtta atttaaaaaa gaaaattagg ctgagagcag tggctcacgc     1620
ctgtaatccc agaactttgg gaggctaagg tgggtggatc acctgaggtc aagagttcca     1680
gaccaggctg gccagcatgg tgaaacccccg tctgtactaa aaatacaaaa aattaactgg    1740
gcatggtagt gggtgcctgt aatcccagct acttgggagg ctgaggtggg agaattgctc     1800
gaacttggag gtgaaggttg tggtgagcca tgatcgcacc actgcactct agcctgggtg     1860
accgagggag gctctgtctc aaaagcaaag caaaaacaaa aacaaaaaca cctaaaaaac     1920
ctgcagtttt gtttgtactt tgttttaaa ttatgctttc tattttgaga tcattgcaaa      1980
ctcaacacaa ttgtaagtaa tgatacagag ggatcttgtg tacccttcac ccagcctccc     2040
ccaatggcaa catcttgcaa aactacaatg tagtctcata accaggatat tgacattgat     2100
acagtgaaga tacaggacat tctcatcacc acagggatcc ccaggatgcc cacttccctc     2160 caccccccaca ccccagccgt gtccctaacc cctggcaacc aggaatccac tctccatttc    2220
tataatgttg tcatttcaag aatgttattc aatggaatca tatagtatgt aacctgtttt     2280
gagcttaaaa aaaagtata catgactttta atgaggaaaa taaaaatgaa tattgaaatg     2340
tt                                                                    2342
```

<210> SEQ ID NO 3
<211> LENGTH: 708
<212> TYPE: DNA
<213> ORGANISM: Artificial Sequence
<220> FEATURE:
<223> OTHER INFORMATION: rabbit-derived antibody nucleotide sequence

<400> SEQUENCE: 3

```
atggcatgcc ctggcttcct gtgggcactt gtgatctcca cctgtcttga attttccatg       60
gctgagctcg tgctgaccca gactccatcg tccgtgtctg cagctgtggg aggcacagtc      120
accatcaatt gccagtccag tcagagtgtt tataataaca acctcttagc ctggtatcag      180
cagaaaccag ggcagcctcc caagctcctg atctaccagg catccactct ggattctggg      240
gtcccatcac gattcaaagg cagtggaact gggacacact tcactctcac catcagcgac      300
ctggagtgtg acgatgctgc cacttactac tgtcaaggcg gttacaacgg taatattgct      360
gctttcggcg gagggaccga ggtggtcgtc gatggtgatc cagttgcacc tactgtcctc      420
```

```
atcttcccac catctgctga tcttgtggca actggaacag tcaccatcgt gtgtgtggcg    480
aataaatact ttcccgatgt caccgtcacc tgggaggtgg atggcaccac ccaaacaact    540
ggcatcgaga acagtaaaac accgcagaat tctgcagatt gtacctacaa cctcagcagc    600
actctgacac tgaccagcac acagtacaac agccacaaag agtacacctg caaggtgacc    660
cagggcacga cctcagtcgt ccagagcttc aacagggggtg actgctga               708
```

<210> SEQ ID NO 4
<211> LENGTH: 236
<212> TYPE: PRT
<213> ORGANISM: Artificial Sequence
<220> FEATURE:
<223> OTHER INFORMATION: rabbit-derived antibody light chain peptide
      sequence

<400> SEQUENCE: 4

```
Met Ala Cys Pro Gly Phe Leu Trp Ala Leu Val Ile Ser Thr Cys Leu
1               5                   10                  15

Glu Phe Ser Met Ala Glu Leu Val Leu Thr Gln Thr Pro Ser Ser Val
            20                  25                  30

Ser Ala Ala Val Gly Gly Thr Val Thr Ile Asn Cys Gln Ser Ser Gln
        35                  40                  45

Ser Val Tyr Asn Asn Asn Leu Leu Ala Trp Tyr Gln Gln Lys Pro Gly
    50                  55                  60

Gln Pro Pro Lys Leu Leu Ile Tyr Gln Ala Ser Thr Leu Asp Ser Gly
65                  70                  75                  80

Val Pro Ser Arg Phe Lys Gly Ser Gly Thr Gly Thr His Phe Thr Leu
                85                  90                  95

Thr Ile Ser Asp Leu Glu Cys Asp Asp Ala Ala Thr Tyr Tyr Cys Gln
            100                 105                 110

Gly Gly Tyr Asn Gly Asn Gly Ile Ala Ala Phe Gly Gly Gly Thr Glu
        115                 120                 125

Val Val Val Asp Gly Asp Pro Val Ala Pro Thr Val Leu Ile Phe Pro
    130                 135                 140

Pro Ser Ala Asp Leu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235
```

<210> SEQ ID NO 5
<211> LENGTH: 9
<212> TYPE: PRT
<213> ORGANISM: Artificial Sequence
<220> FEATURE:
<223> OTHER INFORMATION: derived from SEQ ID NO:4

<400> SEQUENCE: 5

```
Gln Ser Val Tyr Asn Asn Asn Leu Leu
1               5
```

-continued

<210> SEQ ID NO 6
<211> LENGTH: 1368
<212> TYPE: DNA
<213> ORGANISM: Artificial Sequence
<220> FEATURE:
<223> OTHER INFORMATION: rabbit-derived antibody heavy chain nucleotide sequence

<400> SEQUENCE: 6

```
atggcatgcc ctggcttcct gtgggcactt gtgatctcca cctgtcttga attttccatg      60
gctcagtcgg tgaaggagtc cgagggaggt ctcttcaagc cagcggatac cctgacactc     120
acctgcacag tctctggatt ctccgttaat aataagggag tgatgtgggt ccgccaggct     180
ccagggaacg ggctggaatg gatcggaagt attggtatta gtggtagggt aacctatgcg     240
acctgggcga aaagtcgatc caccatcacc agagacacac acttgaacac ggtgactctg     300
aaagtgacca gtctgacagt cgcggacacg gccacatatt tctgcagaat agggagtaac     360
atctggggcc caggcaccct ggtcaccgtc tcctcagggc aacctaaggc tccatcagtc     420
ttcccactgg ccccctgctg cggggacaca cccagctcca cggtgaccct gggctgcctg     480
gtcaaaggct acctcccgga gccagtgacc gtgacctgga ctcgggcac cctcaccaat     540
ggggtacgca ccttcccgtc cgtccggcag tcctcaggcc tctactcgct gagcagcgtg     600
gtgagcgtga cctcaagcag ccagcccgtc acctgcaacg tggcccaccc agccaccaac     660
accaaagtgg acaagaccgt tgcgccctcg acatgcagca agcccacgtg cccacccct     720
gaactcctgg ggggaccgtc tgtcttcatc ttccccccaa aacccaagga caccctcatg     780
atctcacgca ccccgaggt cacatgcgtg gtggtggacg tgagccagga tgaccccgag     840
gtgcagttca catggtacat aaacaacgag caggtgcgca ccgccgcc gccgctacgg     900
gagcagcagt tcaacagcac gatccgcgtg gtcagcaccc tccccatcgc gcaccaggac     960
tggctgaggg gcaaggagtt caagtgcaaa gtccacaaca aggcactccc ggcccccatc    1020
gagaaaacca tctccaaagc cagagggcag ccctggagc cgaaggtcta caccatgggc    1080
cctcccgg aggagctgag cagcaggtcg gtcagcctga cctgcatgat caacggcttc    1140
taccttccg acatctcggt ggagtgggag aagaacggga aggcagagga caactacaag    1200
accacgccgg ccgtgctgga cagcgacggc tcctacttcc tctacagcaa gctctcagtg    1260
cccacgagtg agtggcagcg gggcgacgtc ttcacctgct ccgtgatgca cgaggccttg    1320
cacaaccact acacgcagaa gtccatctcc cgctctccgg gtaaatga              1368
```

<210> SEQ ID NO 7
<211> LENGTH: 455
<212> TYPE: PRT
<213> ORGANISM: Artificial Sequence
<220> FEATURE:
<223> OTHER INFORMATION: rabbit-derived antibody heavy chaing peptide sequence

<400> SEQUENCE: 7

Met Ala Cys Pro Gly Phe Leu Trp Ala Leu Val Ile Ser Thr Cys Leu
1               5                   10                  15

Glu Phe Ser Met Ala Gln Ser Val Lys Glu Ser Glu Gly Gly Leu Phe
            20                  25                  30

Lys Pro Ala Asp Thr Leu Thr Leu Thr Cys Thr Val Ser Gly Phe Ser
        35                  40                  45

Val Asn Asn Lys Gly Val Met Trp Val Arg Gln Ala Pro Gly Asn Gly
    50                  55                  60

Leu Glu Trp Ile Gly Ser Ile Gly Ile Ser Gly Arg Val Thr Tyr Ala
65                  70                  75                  80

Thr Trp Ala Lys Ser Arg Ser Thr Ile Thr Arg Asp Thr Asn Leu Asn
            85                  90                  95

Thr Val Thr Leu Lys Val Thr Ser Leu Thr Val Ala Asp Thr Ala Thr
            100                 105                 110

Tyr Phe Cys Arg Ile Gly Ser Asn Ile Trp Gly Pro Gly Thr Leu Val
            115                 120                 125

Thr Val Ser Ser Gly Gln Pro Lys Ala Pro Ser Val Phe Pro Leu Ala
            130                 135                 140

Pro Cys Cys Gly Asp Thr Pro Ser Ser Thr Val Thr Leu Gly Cys Leu
145                 150                 155                 160

Val Arg Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
            195                 200                 205

Pro Val Thr Cys Asn Val Ala His Pro Ala Thr Asn Thr Lys Val Asp
            210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
            275                 280                 285

Asn Glu Gln Val Arg Thr Ala Arg Pro Pro Leu Arg Glu Gln Gln Phe
290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
            355                 360                 365

Arg Ser Val Ser Leu Thr Cys Met Ile Asn Gly Phe Tyr Pro Ser Asp
            370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
            435                 440                 445

Ile Ser Arg Ser Pro Gly Lys
            450             455

<210> SEQ ID NO 8
<211> LENGTH: 10

```
<212> TYPE: PRT
<213> ORGANISM: Artificial Sequence
<220> FEATURE:
<223> OTHER INFORMATION: derived from SEQ ID NO:7

<400> SEQUENCE: 8

Thr Tyr Phe Cys Arg Ile Gly Ser Asn Ile
1               5                   10
```